(12) United States Patent
Wallace et al.

(10) Patent No.: US 9,005,220 B2
(45) Date of Patent: Apr. 14, 2015

(54) SUTURING DEVICES AND METHODS WITH ENERGY EMITTING ELEMENTS

(75) Inventors: Jeffrey M. Wallace, Saunderstown, RI (US); Peter J. Lukin, Norfolk, MA (US); Jeffrey Kapec, Westport, CT (US); Kazuna Tanaka, Cos Cob, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 1549 days.

(21) Appl. No.: 11/787,822

(22) Filed: Apr. 18, 2007

(65) Prior Publication Data
US 2008/0058798 A1   Mar. 6, 2008

Related U.S. Application Data

(63) Continuation-in-part of application No. 11/525,733, filed on Sep. 22, 2006, now abandoned.

(60) Provisional application No. 60/788,986, filed on Apr. 4, 2006.

(51) Int. Cl.
*A61B 17/04* (2006.01)
*A61B 18/14* (2006.01)
(Continued)

(52) U.S. Cl.
CPC ....... *A61B 17/0469* (2013.01); *A61B 17/00491* (2013.01); *A61B 17/04* (2013.01); *A61B 17/1114* (2013.01); *A61B 18/1492* (2013.01); *A61B 18/24* (2013.01); *A61B 2017/00893* (2013.01); *A61B 2017/1142* (2013.01); *A61B 2017/306* (2013.01); *A61B 2018/00494* (2013.01);
(Continued)

(58) Field of Classification Search
USPC .................. 606/139, 144, 145–148, 151, 157, 606/110–115, 140–143
See application file for complete search history.

(56) References Cited

U.S. PATENT DOCUMENTS

| 453,508 A | 6/1891 | Ruby |
| 730,152 A | 6/1903 | Pitner |

(Continued)

FOREIGN PATENT DOCUMENTS

| DE | 3909999 A1 | 9/1990 |
| EP | 0591991 A2 | 4/1994 |

(Continued)

OTHER PUBLICATIONS

Bard Interventional Products Division, C. R. Bard, Inc., "RapidFire™ Multiple Band Ligator—Information for Use", No. AE1904601/01, Issued Jun. 1996.

(Continued)

*Primary Examiner* — Dianne Dornbusch
*Assistant Examiner* — Alexander Orkin
(74) *Attorney, Agent, or Firm* — Wolf, Greenfield & Sacks, P.C.

(57) ABSTRACT

A device and method of promoting tissue adhesion to reinforce tissue apposition that may include collecting advancing a tissue apposition device to a body cavity having cavity calls, collecting tissue from the cavity walls, passing at least one tissue securement device through the tissue, applying energy to the collected tissue to produce injury to the tissue, and apposing the collected tissue and securing the one or more tissue securement devices. In this illustrative embodiment, the device and method promotes tissue adhesion between one or more portions of tissue, wherein the tissue adhesion may reinforce a tissue apposition.

16 Claims, 31 Drawing Sheets

(51) Int. Cl.
*A61F 2/00* (2006.01)
*A61F 5/00* (2006.01)
*A61N 1/36* (2006.01)
*A61B 17/00* (2006.01)
*A61B 17/11* (2006.01)
*A61B 18/24* (2006.01)
*A61B 17/30* (2006.01)
*A61B 18/00* (2006.01)
*A61N 1/05* (2006.01)

(52) U.S. Cl.
CPC ...... *A61B 2018/0063* (2013.01); *A61F 2/0063* (2013.01); *A61F 5/0086* (2013.01); *A61N 1/36007* (2013.01); *A61N 2001/0582* (2013.01)

(56) References Cited

U.S. PATENT DOCUMENTS

| | | | |
|---|---|---|---|
| 979,342 A | 12/1910 | Schaefer | |
| 1,325,699 A | 12/1919 | Oesterhaus | |
| 1,868,308 A | 7/1932 | Brunfield | |
| 2,170,599 A | 8/1939 | Stricklen | |
| 2,587,364 A | 2/1952 | Mitchell | |
| 2,601,852 A | 7/1952 | Wendt | |
| 2,621,655 A | 12/1952 | Olson | |
| 2,650,593 A | 9/1953 | Weil et al. | |
| 2,880,728 A | 4/1959 | Rights | |
| 3,013,559 A | 12/1961 | Thomas | |
| 3,238,941 A | 3/1966 | Klein et al. | |
| 3,470,875 A | 10/1969 | Johnson | |
| 3,716,058 A | 2/1973 | Tanner | |
| 3,757,781 A | 9/1973 | Smart | |
| 3,760,810 A | 9/1973 | Hoorn | |
| 3,845,771 A * | 11/1974 | Vise | 606/49 |
| 3,845,772 A | 11/1974 | Smith | |
| 3,858,571 A | 1/1975 | Ruldolph | |
| 4,126,124 A | 11/1978 | Miller | |
| 4,144,876 A | 3/1979 | Deleo | |
| 4,164,225 A | 8/1979 | Johnson et al. | |
| 4,210,148 A | 7/1980 | Stivala | |
| 4,216,777 A | 8/1980 | Pridemore | |
| 4,226,239 A | 10/1980 | Polk et al. | |
| 4,234,111 A | 11/1980 | Dischinger | |
| 4,236,470 A | 12/1980 | Stenson | |
| 4,291,698 A | 9/1981 | Fuchs et al. | |
| 4,345,601 A | 8/1982 | Fukunda | |
| 4,414,908 A | 11/1983 | Eguchi et al. | |
| 4,415,092 A | 11/1983 | Boyer | |
| 4,440,171 A | 4/1984 | Nomoto et al. | |
| 4,469,101 A | 9/1984 | Coleman et al. | |
| 4,474,174 A | 10/1984 | Petruzzi | |
| 4,493,319 A | 1/1985 | Polk et al. | |
| D279,504 S | 7/1985 | Tump | |
| 4,597,390 A | 7/1986 | Mulhollan et al. | |
| 4,607,620 A | 8/1986 | Storz | |
| 4,615,472 A | 10/1986 | Nash | |
| 4,621,640 A | 11/1986 | Mulhollan et al. | |
| 4,637,816 A | 1/1987 | Mann | |
| 4,665,906 A | 5/1987 | Jervis | |
| 4,672,979 A | 6/1987 | Pohndorf | |
| 4,706,653 A | 11/1987 | Yamamoto | |
| 4,721,103 A | 1/1988 | Freedland | |
| 4,735,194 A | 4/1988 | Stiegmann | |
| 4,738,255 A | 4/1988 | Goble et al. | |
| 4,741,330 A | 5/1988 | Hayhurst | |
| 4,759,364 A | 7/1988 | Boebel | |
| 4,794,911 A | 1/1989 | Okada | |
| 4,825,259 A | 4/1989 | Berry, Jr. | |
| 4,841,888 A | 6/1989 | Mills et al. | |
| 4,860,746 A | 8/1989 | Yoon | |
| 4,890,615 A | 1/1990 | Caspari et al. | |
| 4,898,156 A | 2/1990 | Gatturna et al. | |
| 4,899,743 A | 2/1990 | Nicholson et al. | |
| 4,923,461 A | 5/1990 | Caspari et al. | |
| 4,927,428 A | 5/1990 | Richards | |
| 4,932,962 A | 6/1990 | Yoon et al. | |
| 4,936,823 A | 6/1990 | Colvin et al. | |
| 4,946,468 A | 8/1990 | Li | |
| 4,950,285 A | 8/1990 | Wilk | |
| 4,968,315 A | 11/1990 | Gatturna | |
| 5,002,042 A | 3/1991 | Okada | |
| 5,002,550 A | 3/1991 | Li | |
| 5,037,021 A | 8/1991 | Mills et al. | |
| 5,037,422 A | 8/1991 | Hayhurst et al. | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,078,731 A | 1/1992 | Hayhurst | |
| 5,080,663 A | 1/1992 | Mills et al. | |
| 5,100,417 A | 3/1992 | Cerier et al. | |
| 5,100,418 A | 3/1992 | Yoon et al. | |
| 5,100,421 A | 3/1992 | Christoudias | |
| 5,102,421 A | 4/1992 | Anspach et al. | |
| 5,116,349 A | 5/1992 | Aranyi | |
| 5,123,913 A | 6/1992 | Wilk et al. | |
| 5,125,553 A | 6/1992 | Oddsen et al. | |
| 5,147,379 A | 9/1992 | Sabbaghian et al. | |
| 5,152,769 A | 10/1992 | Baber | |
| 5,163,945 A | 11/1992 | Ortiz et al. | |
| 5,171,251 A | 12/1992 | Bregen et al. | |
| 5,176,682 A | 1/1993 | Chow | |
| 5,193,525 A | 3/1993 | Silverstein et al. | |
| 5,199,566 A | 4/1993 | Ortiz et al. | |
| 5,203,863 A | 4/1993 | Bidoia | |
| 5,207,679 A | 5/1993 | Li | |
| 5,207,690 A | 5/1993 | Rohrbacher | |
| 5,207,694 A | 5/1993 | Broome | |
| 5,211,650 A | 5/1993 | Noda | |
| 5,213,093 A | 5/1993 | Swindle | |
| 5,217,486 A | 6/1993 | Rice et al. | |
| 5,220,928 A | 6/1993 | Oddsen | |
| 5,224,946 A | 7/1993 | Hayhurst et al. | |
| 5,236,445 A | 8/1993 | Hayhurst et al. | |
| 5,242,431 A | 9/1993 | Kristiansen | |
| 5,254,126 A | 10/1993 | Filipi et al. | |
| 5,258,015 A | 11/1993 | Li et al. | |
| 5,258,016 A | 11/1993 | Dipoto et al. | |
| 5,259,366 A | 11/1993 | Reydel et al. | |
| 5,268,001 A | 12/1993 | Nicholson et al. | |
| 5,269,789 A | 12/1993 | Chin et al. | |
| 5,269,809 A | 12/1993 | Hayhurst et al. | |
| 5,273,053 A | 12/1993 | Pohndorf | |
| 5,281,236 A | 1/1994 | Bagnato et al. | |
| 5,281,237 A | 1/1994 | Gimpelson | |
| 5,282,832 A | 2/1994 | Toso et al. | |
| 5,284,485 A | 2/1994 | Kammerer et al. | |
| 5,290,296 A | 3/1994 | Phillips | |
| 5,290,297 A | 3/1994 | Phillips | |
| 5,297,536 A | 3/1994 | Wilk | |
| 5,304,184 A | 4/1994 | Hathaway et al. | |
| 5,306,280 A | 4/1994 | Bregen et al. | |
| 5,306,309 A | 4/1994 | Wagner et al. | |
| 5,312,438 A | 5/1994 | Johnson | |
| 5,320,630 A | 6/1994 | Ahmed | |
| 5,324,308 A | 6/1994 | Pierce | |
| 5,330,442 A | 7/1994 | Green et al. | |
| 5,330,486 A | 7/1994 | Wilk | |
| 5,333,624 A | 8/1994 | Tovey | |
| 5,334,200 A | 8/1994 | Johnson | |
| 5,336,229 A * | 8/1994 | Noda | 606/144 |
| 5,344,060 A | 9/1994 | Gravener et al. | |
| 5,354,298 A | 10/1994 | Lee et al. | |
| 5,356,413 A | 10/1994 | Martins et al. | |
| 5,356,416 A | 10/1994 | Chu et al. | |
| 5,364,407 A | 11/1994 | Poll | |
| 5,364,408 A | 11/1994 | Gordon | |
| 5,368,599 A | 11/1994 | Hirsch et al. | |
| 5,368,601 A | 11/1994 | Sauer et al. | |
| 5,370,662 A | 12/1994 | Stone et al. | |
| 5,372,599 A | 12/1994 | Martins | |
| 5,372,604 A | 12/1994 | Trott | |
| 5,376,101 A | 12/1994 | Green et al. | |
| 5,380,334 A | 1/1995 | Torrie et al. | |
| 5,383,905 A | 1/1995 | Golds et al. | |

(56) References Cited

U.S. PATENT DOCUMENTS

| | | | |
|---|---|---|---|
| 5,389,103 A | 2/1995 | Melzer et al. |
| 5,391,173 A | 2/1995 | Wilk |
| 5,391,176 A | 2/1995 | Torre |
| 5,391,182 A | 2/1995 | Chin |
| 5,398,844 A | 3/1995 | Zaslavsky et al. |
| 5,403,346 A | 4/1995 | Loeser |
| 5,403,348 A | 4/1995 | Bonutti |
| 5,405,354 A | 4/1995 | Sarrett |
| 5,405,359 A | 4/1995 | Pierce |
| 5,409,499 A | 4/1995 | Yi |
| 5,411,506 A | 5/1995 | Goble et al. |
| 5,411,522 A | 5/1995 | Trott |
| 5,411,523 A | 5/1995 | Goble |
| 5,413,585 A | 5/1995 | Pagedas |
| 5,417,691 A | 5/1995 | Hayhurst |
| 5,417,697 A | 5/1995 | Wilk et al. |
| 5,417,699 A | 5/1995 | Klein et al. |
| 5,423,834 A | 6/1995 | Ahmed |
| 5,423,860 A | 6/1995 | Lizardi et al. |
| 5,431,639 A | 7/1995 | Shaw |
| 5,431,666 A | 7/1995 | Sauer et al. |
| 5,433,722 A | 7/1995 | Sharpe et al. |
| 5,437,680 A | 8/1995 | Yoon |
| 5,439,467 A | 8/1995 | Benderev et al. |
| 5,443,482 A | 8/1995 | Stone et al. |
| 5,445,167 A | 8/1995 | Yoon et al. |
| 5,447,512 A | 9/1995 | Wilson et al. |
| 5,458,608 A | 10/1995 | Wortrich |
| 5,462,545 A | 10/1995 | Wang et al. |
| 5,462,558 A | 10/1995 | Kolesa et al. |
| 5,462,559 A | 10/1995 | Ahmed |
| 5,462,561 A | 10/1995 | Voda |
| 5,464,426 A | 11/1995 | Bonutti |
| 5,466,241 A | 11/1995 | Leroy et al. |
| 5,470,337 A | 11/1995 | Moss |
| 5,474,572 A | 12/1995 | Hayhurst |
| 5,474,573 A | 12/1995 | Hatcher |
| 5,478,353 A | 12/1995 | Yoon |
| 5,487,746 A | 1/1996 | Yu et al. |
| 5,507,754 A | 4/1996 | Green et al. |
| 5,507,758 A | 4/1996 | Thomason et al. |
| 5,507,797 A | 4/1996 | Suzuki et al. |
| 5,514,159 A | 5/1996 | Matula et al. |
| 5,520,700 A | 5/1996 | Beyar et al. |
| 5,520,702 A | 5/1996 | Saur et al. |
| 5,520,703 A | 5/1996 | Essig et al. |
| 5,527,318 A | 6/1996 | McGarry |
| 5,531,763 A | 7/1996 | Mastri et al. |
| 5,542,432 A | 8/1996 | Slater et al. |
| 5,545,170 A | 8/1996 | Hart |
| 5,545,180 A | 8/1996 | Le et al. |
| 5,549,617 A | 8/1996 | Green et al. |
| 5,562,686 A | 10/1996 | Sauer et al. |
| 5,562,689 A | 10/1996 | Green et al. |
| 5,562,720 A | 10/1996 | Stern et al. |
| 5,569,274 A | 10/1996 | Rapacki et al. |
| 5,569,305 A | 10/1996 | Bonutti |
| 5,571,116 A | 11/1996 | Bolanos et al. |
| 5,582,609 A * | 12/1996 | Swanson et al. ............... 606/39 |
| 5,584,861 A | 12/1996 | Swain et al. |
| 5,584,862 A | 12/1996 | Bonutti |
| 5,591,177 A | 1/1997 | Lehrer |
| 5,591,180 A | 1/1997 | Hinchliffe |
| 5,601,530 A | 2/1997 | Neilsen et al. |
| 5,601,571 A | 2/1997 | Moss |
| 5,609,597 A | 3/1997 | Lehrer |
| 5,618,314 A | 4/1997 | Harwin et al. |
| 5,624,453 A | 4/1997 | Ahmed |
| 5,626,590 A | 5/1997 | Wilk |
| 5,630,824 A | 5/1997 | Hart |
| 5,645,553 A | 7/1997 | Kolesa et al. |
| 5,658,313 A | 8/1997 | Thal et al. |
| 5,665,109 A | 9/1997 | Yoon |
| 5,665,112 A | 9/1997 | Thal |
| 5,681,328 A | 10/1997 | Lamport et al. |
| 5,681,351 A | 10/1997 | Jamiolkowski et al. |
| 5,683,417 A | 11/1997 | Cooper |
| 5,683,419 A | 11/1997 | Thal |
| 5,683,464 A | 11/1997 | Wagner et al. |
| 5,688,270 A | 11/1997 | Yates et al. |
| 5,693,060 A | 12/1997 | Martin |
| 5,695,505 A | 12/1997 | Yoon |
| 5,697,940 A | 12/1997 | Chu et al. |
| 5,702,397 A | 12/1997 | Goble et al. |
| 5,720,765 A | 2/1998 | Thal |
| 5,728,136 A | 3/1998 | Thal |
| 5,730,747 A | 3/1998 | Ek et al. |
| 5,735,793 A | 4/1998 | Takahashi et al. |
| 5,735,877 A | 4/1998 | Pagedes |
| 5,741,281 A | 4/1998 | Martin |
| 5,741,301 A | 4/1998 | Pagedes |
| 5,752,963 A | 5/1998 | Allard et al. |
| 5,755,730 A | 5/1998 | Swain et al. |
| 5,782,776 A | 7/1998 | Hani |
| 5,788,715 A | 8/1998 | Watson, Jr. et al. |
| 5,792,153 A * | 8/1998 | Swain et al. ............... 606/144 |
| 5,810,853 A | 9/1998 | Yoon |
| 5,810,854 A | 9/1998 | Beach |
| 5,814,056 A | 9/1998 | Prosst et al. |
| 5,827,298 A | 10/1998 | Hart et al. |
| 5,827,306 A | 10/1998 | Yoon |
| 5,853,416 A | 12/1998 | Tolkoff |
| 5,860,946 A | 1/1999 | Hofstatter |
| 5,897,487 A | 4/1999 | Ouchi |
| 5,899,921 A | 5/1999 | Caspari et al. |
| 5,902,321 A | 5/1999 | Caspari et al. |
| 5,910,105 A | 6/1999 | Swain et al. |
| 5,919,208 A | 7/1999 | Valenti |
| RE36,289 E | 8/1999 | Le et al. |
| 5,931,844 A | 8/1999 | Thompson et al. |
| 5,935,149 A | 8/1999 | Ek |
| 5,938,586 A | 8/1999 | Wilk et al. |
| 5,947,983 A | 9/1999 | Solar et al. |
| 5,972,001 A | 10/1999 | Yoon |
| 5,984,917 A | 11/1999 | Fleischman et al. |
| 5,997,556 A | 12/1999 | Tanner |
| 6,001,110 A | 12/1999 | Adams |
| 6,007,551 A | 12/1999 | Peifer et al. |
| 6,010,515 A | 1/2000 | Swain et al. |
| 6,010,525 A | 1/2000 | Bonutti et al. |
| 6,015,428 A | 1/2000 | Padedas |
| 6,024,755 A | 2/2000 | Addis |
| 6,044,846 A | 4/2000 | Edwards |
| 6,059,719 A | 5/2000 | Yamamoto et al. |
| 6,059,798 A | 5/2000 | Tolkoff |
| 6,066,160 A | 5/2000 | Colvin et al. |
| 6,071,233 A | 6/2000 | Ishikawa et al. |
| 6,071,292 A | 6/2000 | Makower et al. |
| 6,074,401 A | 6/2000 | Gardiner et al. |
| 6,086,600 A | 7/2000 | Kortenbach |
| 6,086,608 A | 7/2000 | Ek et al. |
| 6,099,535 A | 8/2000 | Lamport et al. |
| 6,126,677 A | 10/2000 | Ganaia et al. |
| 6,129,661 A | 10/2000 | Iafrati et al. |
| 6,136,009 A | 10/2000 | Mears |
| 6,149,658 A | 11/2000 | Gardiner et al. |
| 6,159,234 A | 12/2000 | Bonutti et al. |
| 6,165,176 A * | 12/2000 | Barath ............... 606/49 |
| 6,200,329 B1 | 3/2001 | Fung et al. |
| 6,241,140 B1 | 6/2001 | Adams et al. |
| 6,280,452 B1 | 8/2001 | Mears |
| 6,358,259 B1 | 3/2002 | Swain et al. |
| 6,363,937 B1 | 4/2002 | Hovda et al. |
| 6,402,744 B2 | 6/2002 | Edwards et al. |
| 6,436,108 B1 | 8/2002 | Mears |
| 6,514,265 B2 | 2/2003 | Ho et al. |
| 6,551,332 B1 | 4/2003 | Nguyen et al. |
| 6,607,541 B1 | 8/2003 | Gardiner et al. |
| 6,629,630 B2 | 10/2003 | Adams |
| 6,666,844 B1 * | 12/2003 | Igo et al. ............... 604/115 |
| 6,719,763 B2 | 4/2004 | Chung et al. |
| 6,736,828 B1 | 5/2004 | Adams et al. |
| 7,083,615 B2 * | 8/2006 | Peterson et al. ............... 606/41 |
| 7,794,461 B2 * | 9/2010 | Eder et al. ............... 606/51 |

(56) References Cited

U.S. PATENT DOCUMENTS

| | | |
|---|---|---|
| 2002/0177847 A1 | 11/2002 | Long |
| 2003/0167062 A1 | 9/2003 | Gambale et al. |
| 2003/0171651 A1 | 9/2003 | Page et al. |
| 2003/0171760 A1 | 9/2003 | Gambale |
| 2003/0176880 A1 | 9/2003 | Long et al. |
| 2003/0208209 A1 | 11/2003 | Gambale et al. |
| 2003/0236535 A1* | 12/2003 | Onuki et al. ............ 606/144 |
| 2004/0034371 A1 | 2/2004 | Lehman et al. |
| 2004/0138704 A1 | 7/2004 | Gambale et al. |
| 2004/0158125 A1 | 8/2004 | Aznoian et al. |
| 2004/0193147 A1* | 9/2004 | Malecki et al. ............ 606/32 |
| 2005/0033319 A1 | 2/2005 | Gambale et al. |
| 2006/0074410 A1* | 4/2006 | Malecki et al. ............ 606/32 |
| 2007/0129735 A1* | 6/2007 | Filipi et al. ............ 606/144 |

FOREIGN PATENT DOCUMENTS

| | | |
|---|---|---|
| EP | 0598219 A2 | 5/1994 |
| GB | 2165559 | 4/1986 |
| JP | 7-136177 | 5/1995 |
| WO | WO 96/09796 | 4/1996 |
| WO | WO 96/20647 | 7/1996 |
| WO | WO 99/22650 | 5/1999 |
| WO | WO 99/52423 A1 | 10/1999 |
| WO | WO 99/59486 A2 | 11/1999 |
| WO | WO 99/66844 | 12/1999 |
| WO | WO 01/66001 | 9/2001 |
| WO | WO 01/66018 A1 | 9/2001 |
| WO | WO 01/87144 | 11/2001 |
| WO | WO 01/89370 A2 | 11/2001 |
| WO | WO 01/89393 | 11/2001 |

OTHER PUBLICATIONS

Cook® Wilson-Cook Medical GI Endoscopy, Sales Literature, www.wilsoncook.com.

Communication from the European Patent Office for European Application No. EP 08 743 116, dated Aug. 13, 2010.

S. Sherman et al., "Efficacy of Endoscopic Sphincterotomy and Surgical Sphincteroplasty for Patients with Sphincter of Oddi Dysfunction: Randomized, Prospective Study", *Gastrointest Endosc*, vol. 37, No. 2, 1991, p. 249 (Abstract).

S. Sherman et al. "Endoscopic Sphincterotomy Induced Hemorrhage: Treatment with Multipolar Electrocoagulation", *Gastrointest Endosc*, vol. 37, No. 2, 1991, p. 249 (Abstract).

G. Lehman et al., "Endoscopic Gastroesophageal Suturing: Does Addition of Cautery Aid Plication Persistence?" *Digestive Disease Week* Poster Board Presentation—May 2000, On-line Abstract Feb. 2000.

C. J. Filipi, Transoral, Flexible Endoscopic Suturing for Treatment of GERD: A Multicenter Trial, *Gastrointest Endosc* Apr. 2001; 53(4): 416-422.

T. Martinez-Sema et al., Endoscopic Valvuloplasty for GERD, Gastrointest Endosc Nov. 2000; 52 (5): 663-70.

* cited by examiner

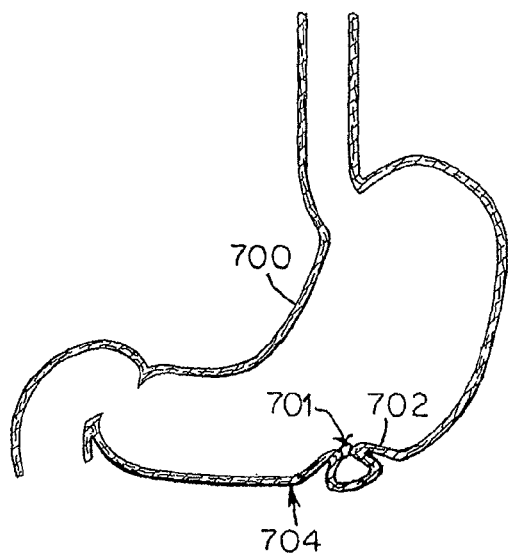
Fig. 23A
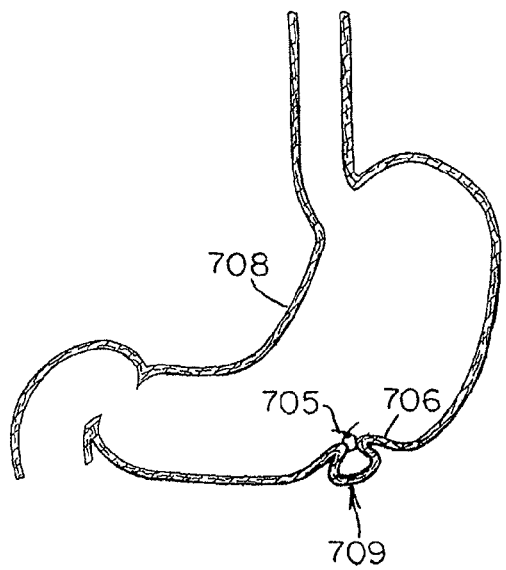
Fig. 23B
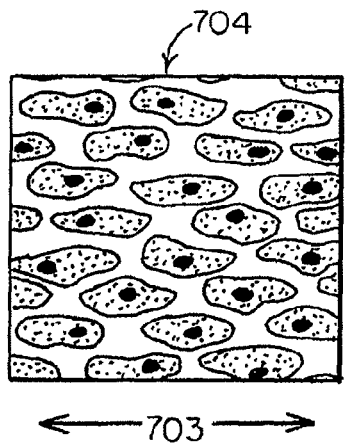
Fig. 23A1
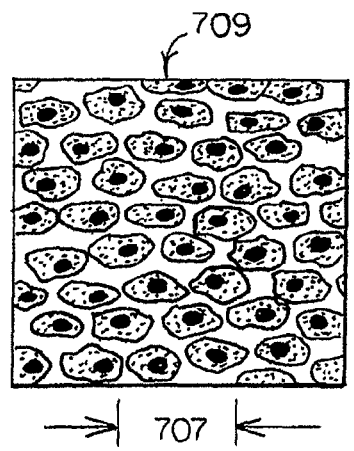
Fig. 23B1

SUTURING DEVICES AND METHODS WITH ENERGY EMITTING ELEMENTS

This application is a continuation-in-part of U.S. application Ser. No. 11/525,733, filed Sep. 22, 2006, now abandoned, which claims priority to U.S. Provisional Application Ser. No. 60/788,986, filed Apr. 4, 2006. The content of each application number listed above are hereby incorporated by reference in their entirety.

FIELD OF INVENTION

This present invention relates to devices and methods for performing restriction or alterations within a body cavity that may lead to weight loss.

BACKGROUND

Obesity, as defined by a body mass index (BMI) of 30 kg/m² or more, is a rapidly growing problem, currently affecting more than 30% of adults in the United States. Morbid obesity, as defined by a body mass index of 40 kg/m² or more or a BMI of 35 kg/m² or more in the presence of co-morbidities is also prevalent, affecting 3.1% of men and 6.7% of women. Obesity is commonly associated with many serious medical disorders including heart disease, diabetes, hypertension, hyperlipidemia, hypercholesterolemia, osteoarthritis and sleep apnea. In addition, approximately 300,000 adults in the U.S. die each year due to obesity-related causes.

The primary treatment objective for obese patients is weight reduction, which can improve co-morbid conditions and also reduces risk factors for disease. Even moderate weight loss (5%-10% of initial weight) produces health benefits and has been associated with marked reductions in the risk for the medical disorders listed above. While non-operative and pharmacologic weight loss therapies have met with only limited success, surgical intervention for morbid obesity, most frequently gastric bypass, is becoming increasingly common. However, the decision to undergo gastric bypass is a difficult one. Patients who choose to undergo gastric bypass are making a serious commitment to permanent life-style changes and are at risk for developing metabolic/nutritional complications resulting from the long-term malabsorptive effects of gastric bypass and food intake restriction. Long-term complications of gastric bypass including anemia secondary to iron or $B_{12}$ deficiency, mineral deficiencies (hypokalemia and hypomagnesia) and bone disease associated with secondary hyperparathyroidism are not uncommon. These conditions can be serious thereby necessitating life-long medical follow-up to monitor for such events.

Although various procedures exist for the surgical treatment of morbid obesity, the Roux-en-Y gastric bypass (RYGB) has been identified as the gold standard for morbidly obese patients when non-invasive interventions have failed. The RYGB procedure entails the creation of a small gastric pouch to which the distal jejunum is attached via creation of an anastomosis referred to as a gastrojejunostomy (GJ). The procedure excludes more than 95% of the stomach, all of the duodenum and the proximal jejunum from digestive continuity. Weight loss is thought to result from reduced intake volume due to the small gastric pouch and limited GJ diameter, as well as from malabsorption due to the bypass of the proximal jejunum. The procedure is associated with a mean of 65-75% excess weight loss with 1% mortality and 10% morbidity.

Despite the favorable safety and effectiveness profile of the RYGB procedure, technical complications and inadequate weight loss may occur. Serious complications are not uncommon after open bariatric procedures. Adhesion formation may contribute to small bowel obstructions, which may require an additional operation for the patient. Incisional hernias are another complication associated with abdominal surgical procedures and have been shown to occur at a much higher rate after open gastric bypass surgery than after laparoscopic bypass surgery.

The significant morbidity associated with traditional weight loss surgery emphasizes the importance of the development of minimally invasive interventions that will result in patient weight loss, which may improve co-morbid conditions and also reduce risk factors for disease. Additionally, a minimally invasive or intragastrointestinal approach will minimize or eliminate many of the risks associated with open and laparoscopic procedures.

BRIEF DESCRIPTION OF THE DRAWINGS

Certain embodiments of the invention are described with reference to the accompanying drawings, which, for illustrative purposes, are not necessarily drawn to scale.

FIG. 23 is an illustration that demonstrates stretching and/or compression of tissue resulting from a tissue apposition.

DETAILED DESCRIPTION

The present invention provides methods for the apposition of tissue between two or more tissue surfaces. The embodied methods may be useful for external or internal tissue regions, but may be especially useful in endoscopic procedures. One example of such an endoscopic procedure is the endoscopic suturing of gastrointestinal tissue to reduce the volume, capacity, or function of the gastrointestinal cavity as a possible treatment for obesity. Another example of such an endoscopic procedure is the endoscopic suturing of gastrointestinal tissue to close or reduce a fistula. U.S. Pat. Nos. 4,841,888, 5,037,021, 5,080,666, 5,792,153, and U.S. patent application Ser. No. 10/847,190 describe endoscopic suturing systems and methods with which the present invention is useful or may be used. Those patents and patent applications are incorporated by reference herein, in their entirety. A brief description of the basic elements of the endoscopic suturing systems and methods is presented below and the description of the illustrative embodiments will focus on the methods of the present invention as it is preferably used in endoscopic procedures.

Figure 1:
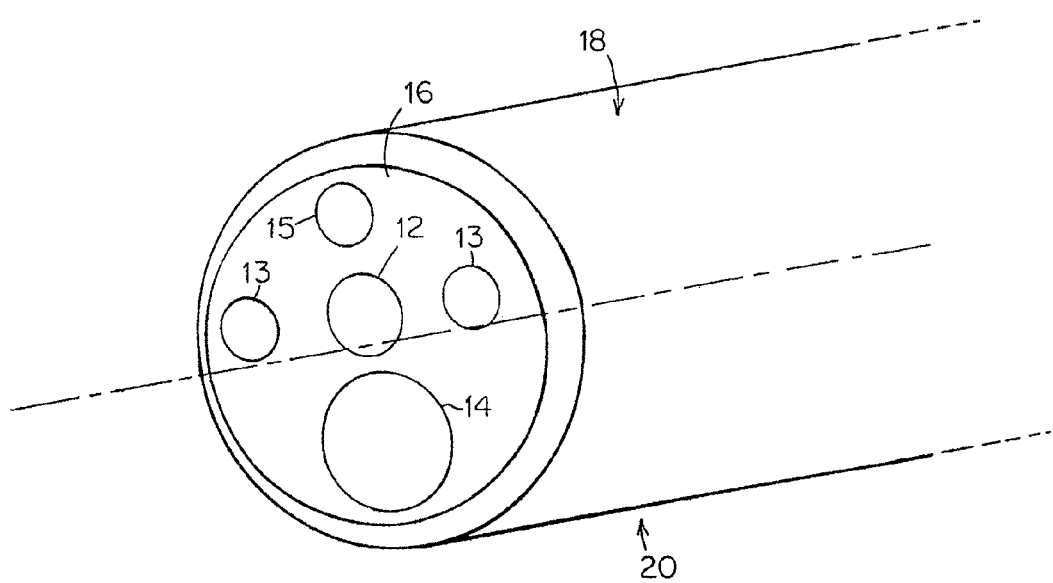
FIG. 1 is a diagrammatic illustration of a distal end of an endoscope.

FIG. 1 shows the distal end 18 of a flexible endoscope 20 with which the present invention may be used. Terminating at a distal face 16 of the endoscope are several channels through which various functions may be performed. Typically, at least one large working channel lumen 14 is provided through which various medical instruments, catheters or accessory control mechanisms may be passed. In the case of viewing endoscopes, a viewing lens 12 is provided on the distal face of the endoscope to permit viewing via optical fibers or digital electronics that extend from the lens of the endoscope to its proximal end. Lights 13 illuminate the treatment site so that it may be viewed through the lens 12. Some endoscopes also have a fluid port 15 through which solution may be passed under pressure to rinse the lens of biological debris during a procedure. Additionally, a fluid port 15 may be used to transport fluid into the treatment site.

Figure 2:
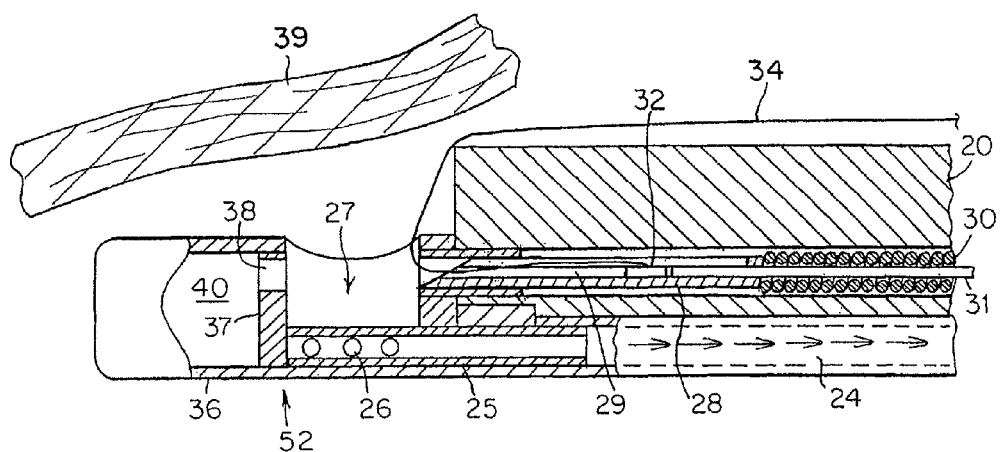
FIG. 2 is a partial sectional side view of a prior art endoscopic tissue apposition device.
Figure 3:
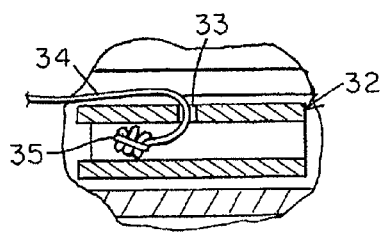
FIG. 3 is a diagrammatic illustration of an embodied thread carrier where the suture material is fixated to a thread carrier.
Figure 4:
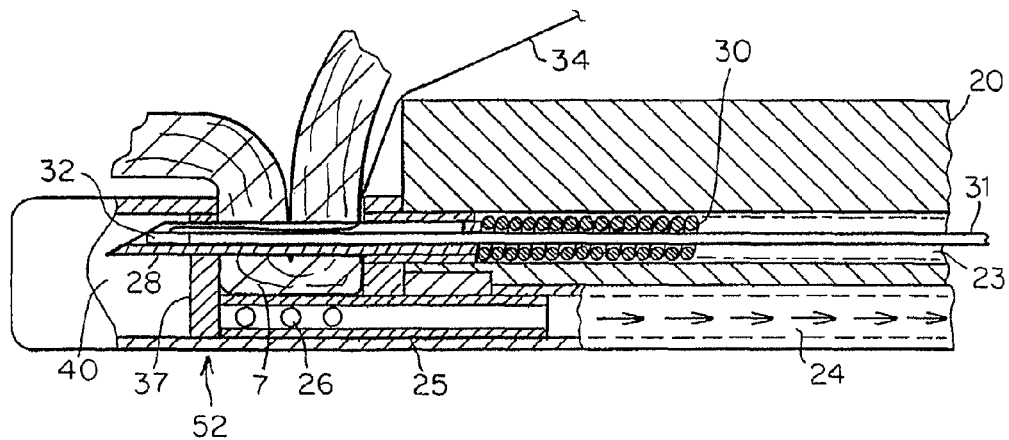
FIG. 4 and FIG. 5 are partial sectional views of a prior art endoscopic tissue apposition device placing a suture through a fold of tissue.

FIG. 2-4 depict a prior art endoscopic tissue apposition device disclosed in U.S. Pat. No. 5,792,153. FIG. 2 shows the distal end of a flexible endoscope 20, on which a sewing device 52 is attached. As mentioned above, the endoscope is provided with a viewing channel, which is not shown, but which terminates at a lens 12 on the distal face of the endoscope. The endoscope is further provided with a biopsy/working channel 14, and a suction channel 24, the proximal end of which is connected to a source of reduced pressure (not shown). The sewing device 52 has a tube 25, which communicates with the suction pipe 24 and may have a plurality of perforations 26 therein. These perforations communicate with an upwardly open cavity 27 formed in the sewing device that may be embodied as a vacuum chamber.

A hollow needle 28 is mounted in the biopsy channel 14, with its beveled tip extending into the sewing device. The needle has a channel 29 extending therethrough. A flexible, wire-wound cable 30 has its forward end attached to the rear of the needle 28, and a center wire 31 runs within the cable 30, along the entire length thereof, and is longitudinally movable with respect thereto. The diameter of the wire 31 is such that it is longitudinally movable within the channel 29 and, in the position shown in FIG. 2, the forward end portion of the wire 31 extends into the rear end portion of the channel 29.

A thread carrier in the form of a tag 32 is mounted in the channel 29. The tag is shown in more detail in FIG. 3. The tag may be hollow and may have an aperture 33 extending through the side-wall thereof. As can also be seen in FIG. 3, one end of the thread 34 is secured to the tag by passing it through the aperture 33 and fixating the thread within the tag. One embodiment of the fixating the thread within the tag is illustrated in FIG. 3 by passing the thread through the aperture and tying in the end of a knot 35 of sufficient size to prevent the thread from escaping from the tag.

The sewing device has a hollow head portion 36 defining a chamber 40 therein, with the head portion 36 and the endoscope 20 being on opposite sides of the cavity 27. Between the chamber 40 and the cavity 27 is a wall 37, in which there is formed an aperture 38. The aperture 38 has a diameter that is marginally greater than the external diameter of the needle 28 and the aperture 38 must be sufficiently small to prevent tissue from being forced through the aperture and causing the needle to jam. Finally, FIG. 2 shows a portion of the patient's tissue 39, in which a stitch is to be formed.

In operation, suction is applied to the suction pipe 24, and hence, via the perforations 26 in the tube 25 to the cavity 27. This sucks into the cavity a U-shaped fold 7 of the tissue 39 as shown in FIG. 4. The hollow needle 28 is pushed through the U-shaped tissue fold 7 by exerting a distal (leftward) force on the center wire 31. After full advancement of the needle, the tip portion of the needle 28 is on the left-hand side of the wall 37, within the chamber 40 in the hollow head portion 36, and the tag 32, within the channel 29, lies to the left of the wall 37.

Figure 5:
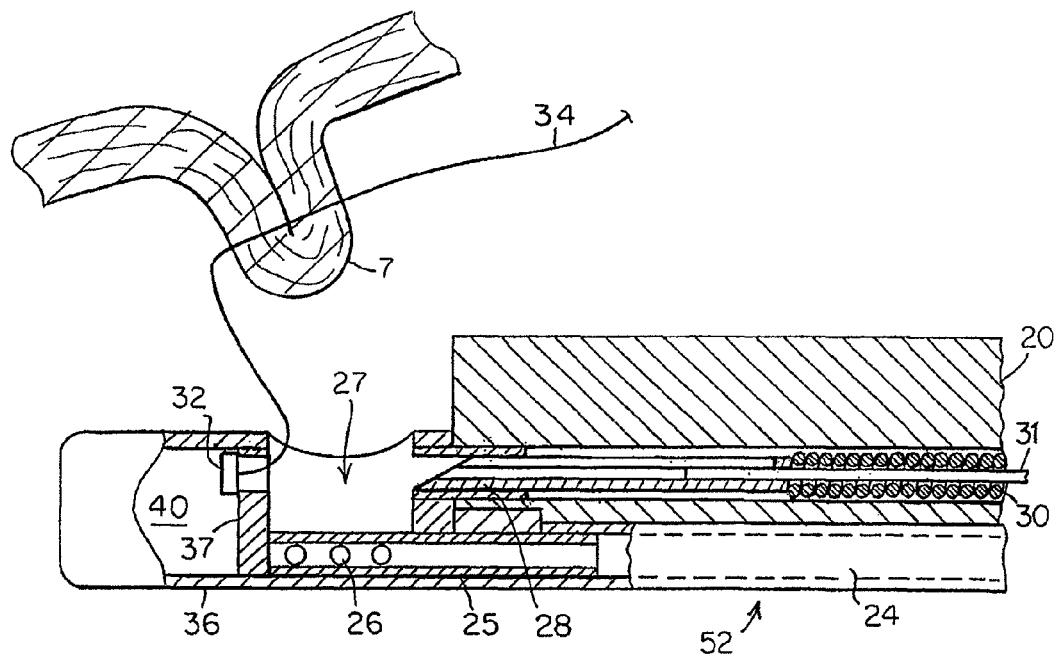

Continued distal movement of the wire 31 pushes the tag 32 out of the channel 29 and into the chamber 40. The wire 31 is then withdrawn proximally (rightwardly), followed by the proximal withdrawal of the cable 20, to bring both back to the positions which they occupy in FIG. 2. The suction is then discontinued allowing the U-shaped tissue fold 7 to be released from the cavity 27. The position is then as shown in FIG. 5. Finally, the endoscope and sewing device are withdrawn from the patient. In so doing, the thread 34 is pulled partially through the tissue fold 7, since the tag 32 is trapped in the chamber 40. The end result is that both ends of the thread are outside of the tissue and can be knotted and/or severed as may be appropriate. It should be noted that a multiple stitch embodiment is also disclosed in U.S. Pat. No. 5,792,153.

Figure 6:
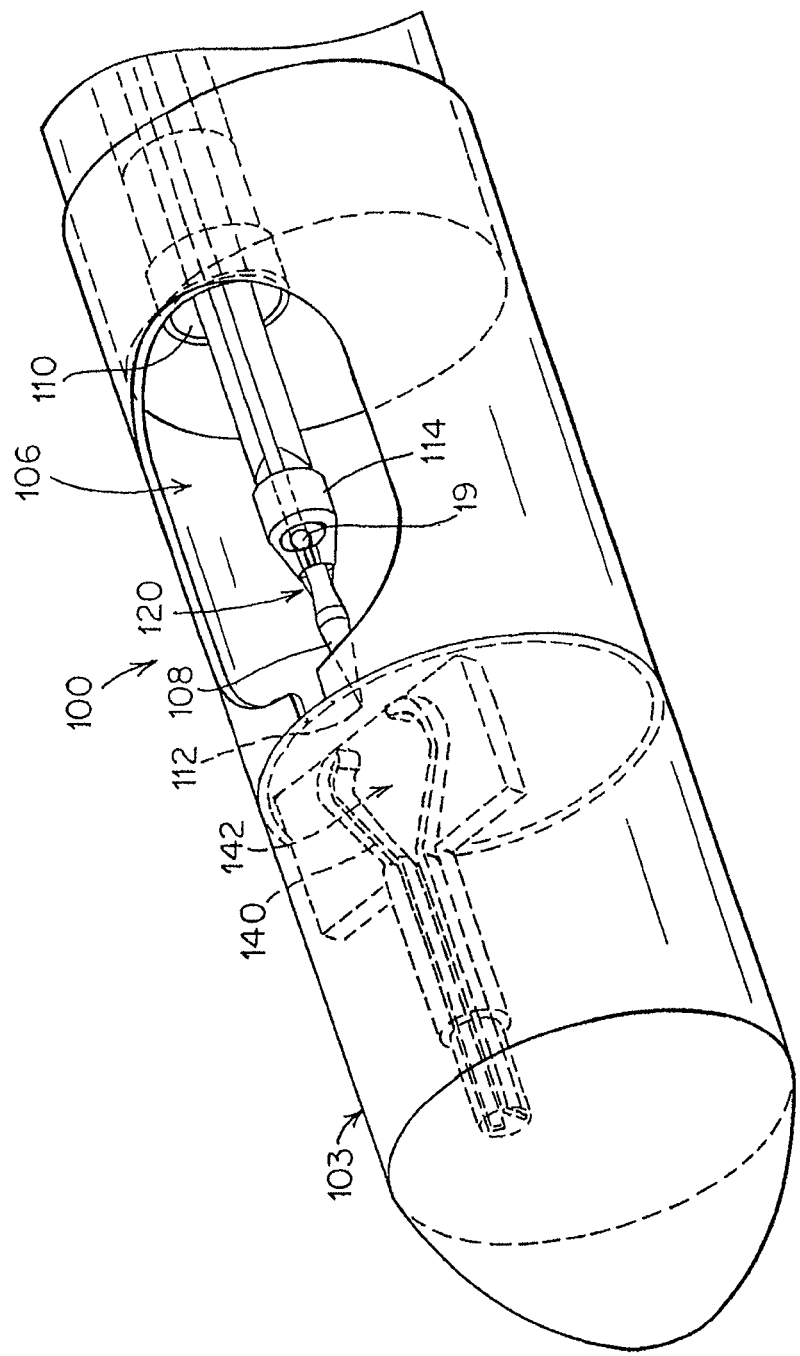
FIG. 6 is an isometric transparent view of a prior art single intubation, multi-stitch endoscopic tissue apposition device.
Figure 7A:
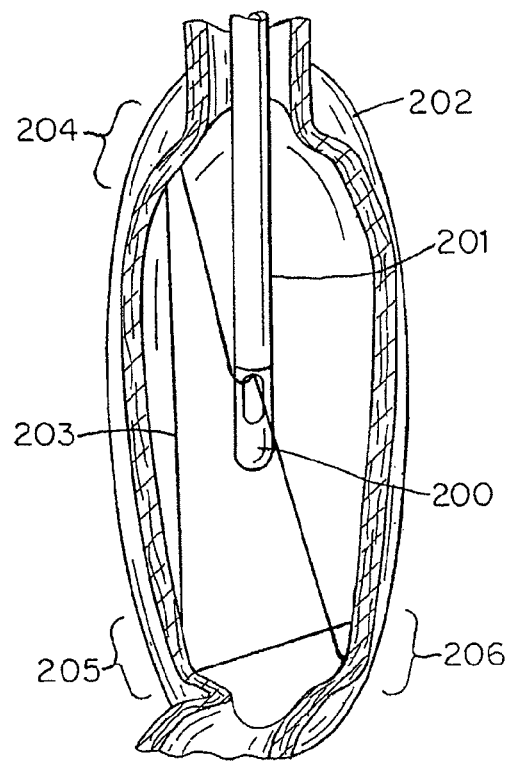
FIG. 7 through FIG. 10 are illustrations of an endoscopic tissue apposition device placing a continuous suture pattern to accomplish tissue apposition.
Figure 7B:
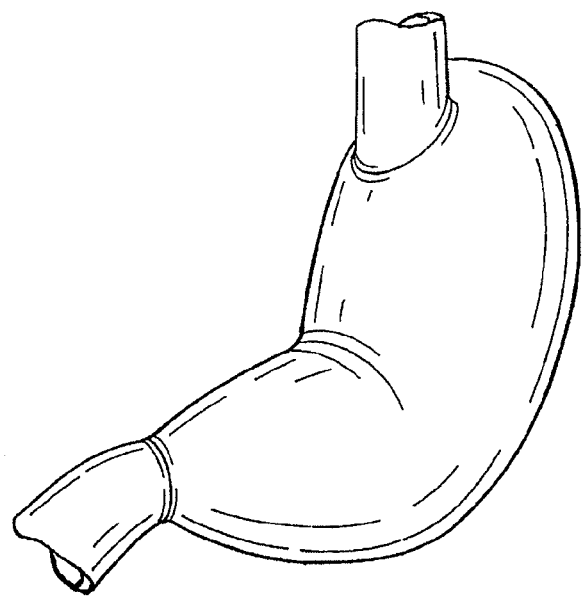

FIG. 6 depicts an embodiment of a prior art tissue apposition device capable of securing multiple tissue sites together with only one intubation of an endoscope carrying a suturing capsule at its distal end into the patient. A comprehensive discussion of the mechanisms associated with the tissue apposition device embodied in FIG. 6 is presented in pending U.S. application Ser. No. 10/847,190, incorporated by reference herein. The single intubation, multi-stitch endoscopic suturing system shown in FIG. 6, includes a suturing capsule 100 positioned at the distal end of an endoscope. The capsule is configured to receive a needle 108 slidable through a needle track 110 formed through the capsule. The needle may be a solid stainless steel shaft with a sharpened distal tip 112 and be joined at its proximal end to a pusher shaft (not shown) that extends proximally from the suture capsule, through the working channel of the endoscope. When the needle is moved longitudinally through the needle track, it traverses the suction chamber 106 so that tissue suctioned into the chamber will be penetrated by the distally advancing needle.

The needle 108 may carry an annular suture tag 114 that fits closely about the outside surface of the needle. Joined to the suture tag is one end of a suture 19 that will be carried through a suctioned tissue portion when the needle carrying the suture tag 114 is advanced distally. The suture tag is releasably and selectively secured to the outside surface of the needle by a suture tag lock 120. Full distal advancement of the needle places the suture tag 114 within the confines of a suture tag catch 140. After penetrating a captured tissue portion and entering the suture catch, the suture tag lock 120 may be released and the needle withdrawn proximally leaving behind the suture tag 114 in a nest area 142 of the suture tag catch. After capture and release of the suture tag into the suture tag catch 140, the needle may be withdrawn proximally and the tissue released from the suction chamber 106 with a suture 19 left passing through the tissue and having one end joined to the captured suture tag at the distal end 103 of the capsule and the other end of the suture extending into the needle track 110, through the working channel of the endoscope and exiting the proximal end of the endoscope.

The steps for retrieval of the tag are substantially the reverse of the steps illustrated for delivering the tag to the suture catch. Once the tissue is released from the capsule the tag may be recaptured by the needle in readiness for another stitch through either the same or a different captured tissue portion. By shuttling the tag and its associated suture through a series of captured tissue portions in this fashion, a plurality of stitches can be formed without requiring removal of the capsule for reloading.

Some embodiments described herein may utilize a vacuum chamber or suction to pull at least a portion of tissue within a chamber or within a path a tissue securement device may pass when it is deployed. In embodiments that comprise suturing as at least part of the tissue securement device, the suction or vacuum may pull the at least a portion of tissue within the path of a needle attached to the suture material such that the suture material may be advanced through said tissue portion. Other embodiments are certainly possible, wherein a mechanical grasper or mechanical device may be used to pull at least a portion of tissue within a chamber or within a path the tissue securement device may pass when it is deployed.

In embodiments comprise suturing or stitching as at least a portion of the tissue securement device, various embodiments of the invention are possible, wherein partial thickness stitches are placed. In other embodiments, full thickness stitches may be placed. Therefore, in embodiments which may comprise suturing where a tissue fold is collected by a tissue apposition device, one or more stitches placed by the tissue apposition device may be either partial thickness or full thickness stitches.

Using a preferred embodiment of a tissue apposition device, a plurality of methods are described below to appose and join internal tissue together, in a manner that may result in altering volume, capacity, or function of a body cavity. A body cavity may be defined as any opening or space within a patient's body that is accessible by endoscopic or laparoscopic devices. Examples of body cavities may include, but are not limited to, oral cavity, esophagus, stomach, small intestines, colon and rectum. A preferred embodiment of the invention utilizes a tissue apposition device within the stomach to alter the volume, capacity, or function of the stomach. By limiting the capacity of the stomach, a patient may not be able to eat as much food, thus potentially causing a reduction in the patient's food intake. This reduction in food intake may result in weight loss of the patient. Additionally, changes in at least a portion of stomach's function may result in an alteration of the patient's food intake, which may result in weight loss. Additional embodiments utilize a tissue apposition device to at least partially close or reduce one or more fistulas within the gastrointestinal tract.

The present embodiments of the invention may utilize one or more tissue securement devices to at least partially accomplish tissue apposition and joining of internal tissue. Examples of tissue securement devices may include, but are not limited to, one or more suture materials, one or more staples, one or more magnets, one or more pins, one or more rods, or a combination thereof. A tissue securement device may comprise a combination of the aforementioned devices as well. One or more tissue securement devices may be comprised within a tissue apposition device, wherein the tissue apposition device may appose and join portions of internal tissue together.

FIG. 7 through FIG. 10 illustrate an embodiment of the present invention utilizing suturing to alter the volume, capacity, or function of the stomach. In FIG. 7A, a tissue apposition device 200 that is mounted on an endoscope 201 is positioned within the lumen of the stomach 202. In this embodiment, the tissue apposition device places stitches into the substantial vicinity of a plurality of tissue sites (204, 205, 206), whereby a suture 203 passes through at least a portion of tissue within the substantial vicinity of the respective tissue sites. The tissue apposition device begins by first placing a tissue securement device into the tissue and passing the suture 203 through the tissue in the substantial vicinity of a first tissue site 204. The device is then navigated to a second tissue site 205 and a second stitch is placed passing the suture through tissue in the substantial vicinity of the second tissue site. Following this, the tissue apposition device may be repositioned to a third tissue site 206. A third stitch may be placed and the suture passed through the tissue in the substantial vicinity of the third tissue site. (The steps to place the stitches are not demonstrated in FIG. 7A) FIG. 7B illustrates an external illustration of the stomach as the tissue apposition device places stitches at the tissue sites 204, 205, 206.

Figure 8A:
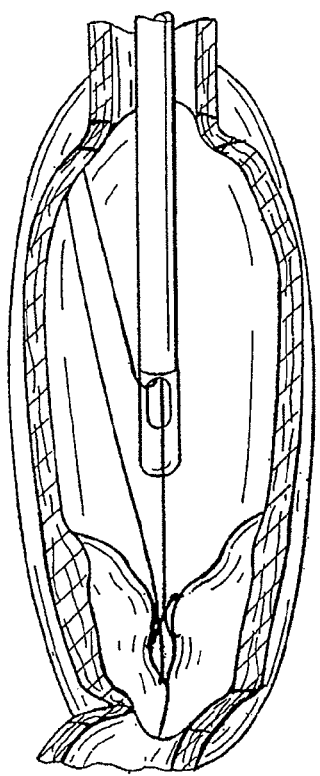
Figure 8B:
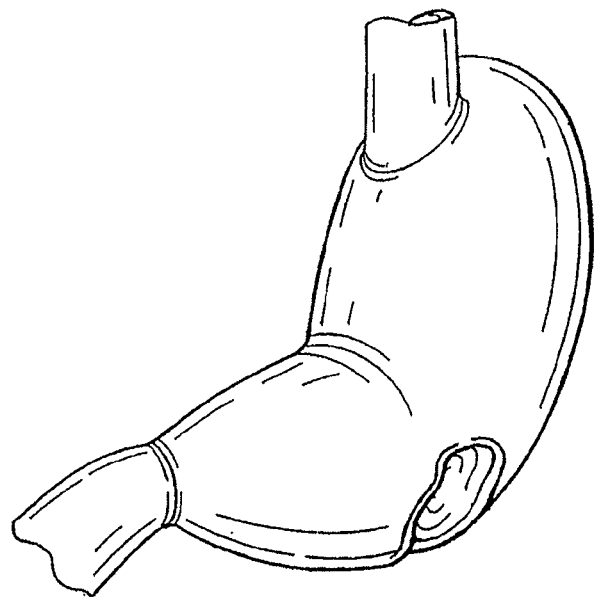

As the embodied tissue apposition device continues to place stitches at tissue sites, the tissue sites may reside on opposing walls of the cavity (for example, tissue sites 205 and 206 are on opposing walls). Through the embodied method, the opposing walls of the cavity may begin to approximate as the suture is drawn tight. The tissue approximation of opposing walls is illustrated in FIG. 8A. Furthermore, as the opposing walls are apposed together, the volume, capacity, or function of the body cavity may be altered. This is illustrated in FIG. 8B, where the tissue sites on opposing walls are being approximated when the suture is pulled tight.

Figure 9:
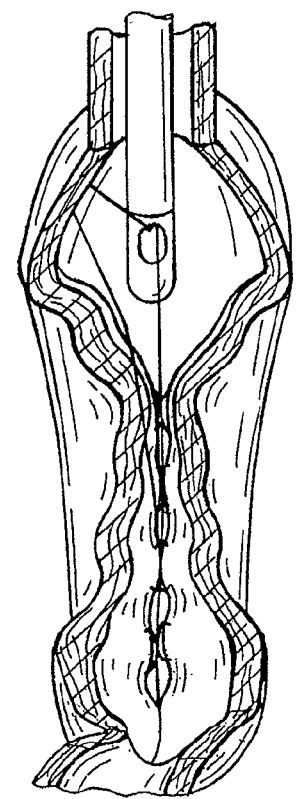
Figure 9:
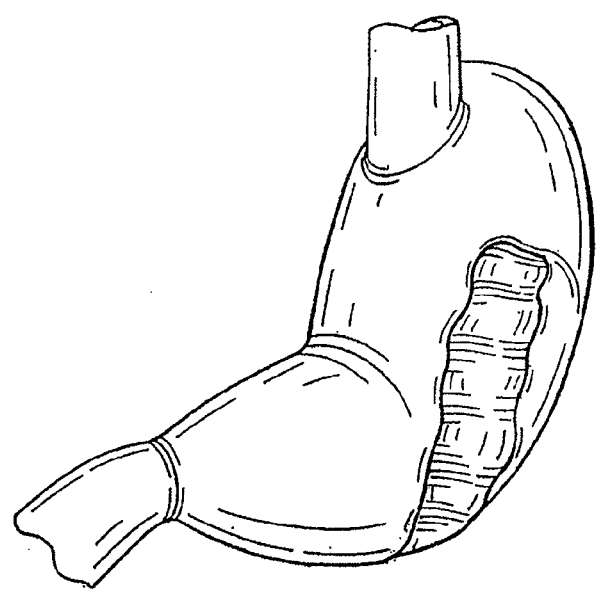
Figure 10:
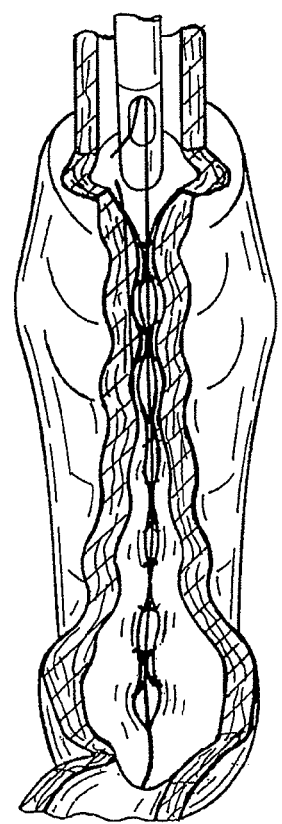
Figure 10:
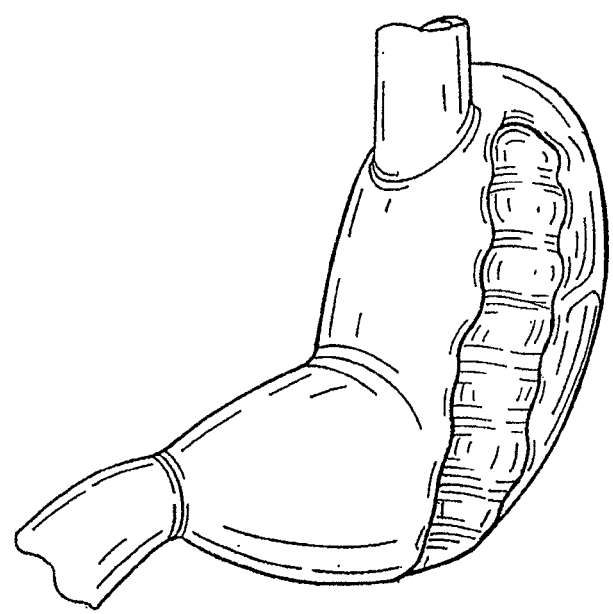
Figure 11A:
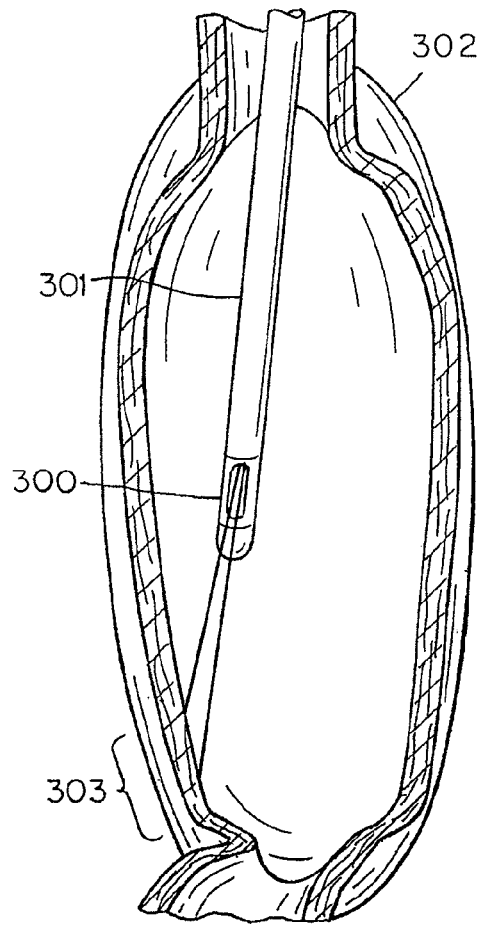
FIG. 11 is an illustration of an endoscopic tissue apposition device placing an interrupted suture stitch to approximate two opposing sections of wall tissue together.
Figure 11B:
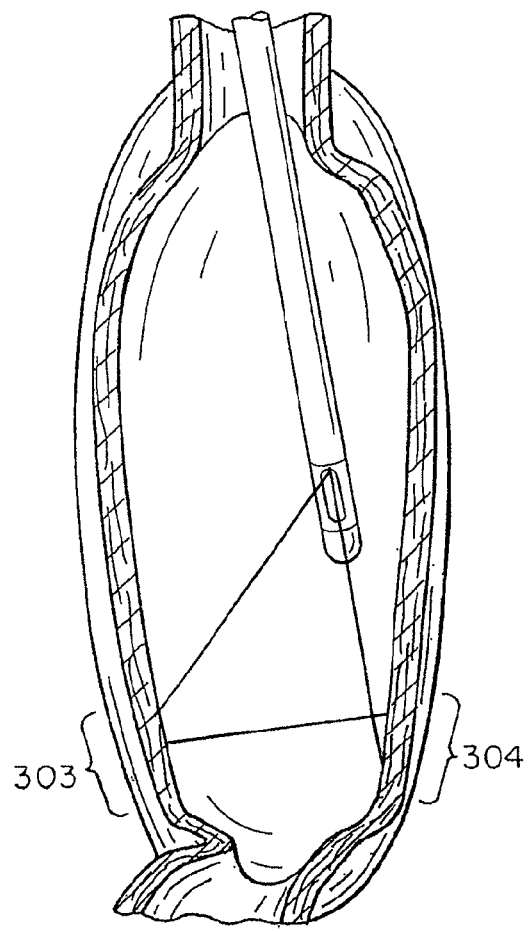
Figure 11C:
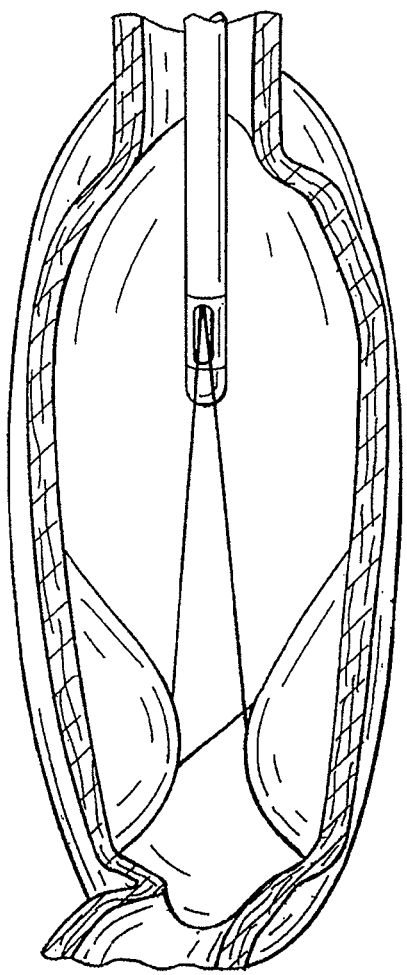
Figure 11D:
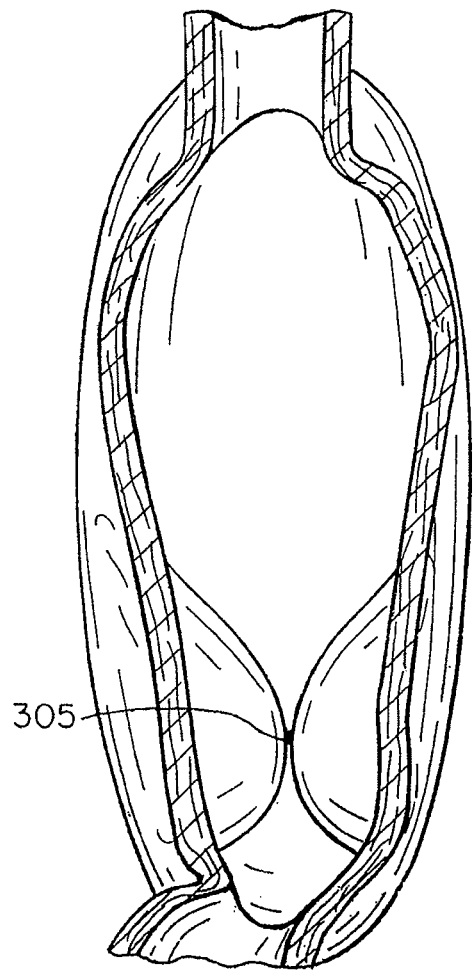

FIG. 9 and FIG. 10 illustrate a continuation of the tissue apposition process as the tissue apposition device sutures from a distal portion of the stomach to a proximal portion of the stomach. As more stitches are placed and more of the opposing cavity walls are approximated, the volume, capacity, or function may continue to be altered. FIG. 10 illustrates the state of the stomach after the embodied method has been completed. The tissue apposition was accomplished in a linear fashion in the direction of distal to proximal. After placing all the sutures as appropriate, the suture may be pulled tight and can be fixated with a method including, but not limited to, a knot or a suture lock device, following which the suture may be severed as may be appropriate.

The preferred embodiments illustrated in FIG. 7 through FIG. 10 demonstrate tissue apposition to alter the volume, capacity, or function of the stomach using a continuous suture stitch method. Other embodiments of the invention are also possible, including the use of different stitch methods. These stitch methods may include, but are not limited to, continuous, interrupted, and figure of eight stitches. Combinations of stitch methods are also possible.

FIG. 11 illustrates an alternate embodiment that may make use of interrupted stitches to approximate the walls of the cavity. The tissue apposition device 300, which is mounted on an endoscope 301 is positioned within a stomach cavity 302. As shown in FIG. 11A, the tissue apposition device is navigated to the distal portion of the stomach and a stitch is placed at a first tissue site 303 by passing the suture through tissue in the vicinity of the first tissue site 303. Following this, as shown in FIG. 11B, the tissue apposition device is repositioned to a second tissue site 304, preferable on an opposing wall of the cavity. At the second tissue site, a stitch is placed and the suture is passed through tissue in the vicinity of the second tissue site 304. The suture is then pulled tight, as illustrated in FIG. 11C, whereby the tissue sites approximate and appose. The suture may then be fixated 305 with a method including, but not limited to, tying a knot or applying a suture lock device, following which the suture may be severed as may be appropriate shown in FIG. 11D. If the tissue sites are located on opposing walls from one another, the tissue apposition may cause the walls to be pulled in, thereby altering the volume, capacity, or function of the body cavity. The embodied method utilized a tissue apposition device comprising suturing, but other embodiments utilizing other tissue securement devices are certainly possible.

Figure 12:
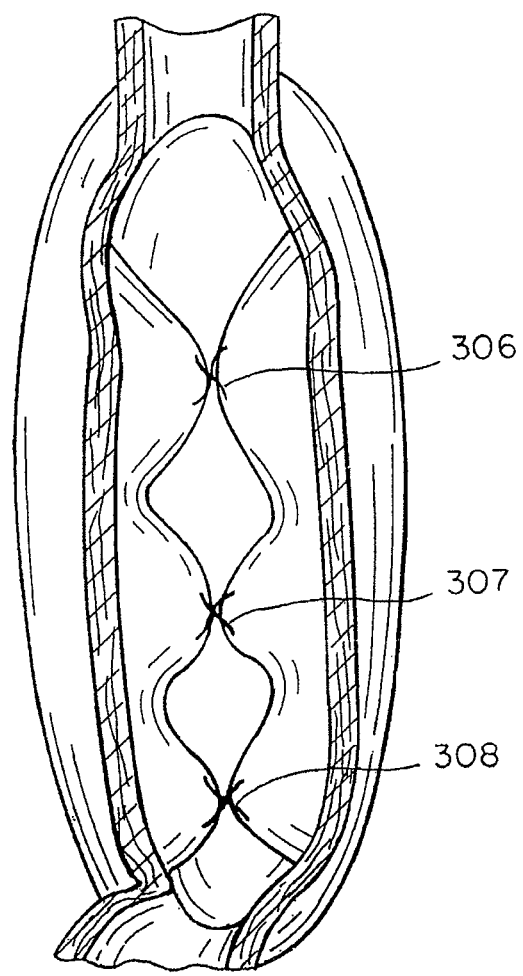
FIG. 12 is an illustration of a series of interrupted suture stitches placed in a pattern to accomplish tissue apposition.

FIG. 12 demonstrates an embodiment of a series of suture stitches being placed in a manner akin to the embodied method illustrated in FIG. 11. Three suture stitches 306, 307, 308 are displayed in FIG. 12 for illustration purposes only, as a plurality of stitches may be possible. Stitches are preferably placed by the tissue apposition device in a series from a distal portion of the stomach to a proximal portion of the stomach. The total number of suture stitches that may be placed may vary based on one or more potential factors including, but not limited to the size of the stomach, the amount of cavity volume/function to be altered as appropriate, the location of the stitches, and the amount of tension caused by pulling the suture tight, or a combination thereof.

In preferred embodiments of the invention, tissue apposition may be accomplished by a series of linearly placed tissue securement devices as illustrated in FIG. 10, FIG. 11, and FIG. 12 (which utilize suture stitches as a tissue securement device). While the embodiments described herein demonstrate the placement of tissue securement devices in a distal to proximal linear direction, other embodiments are certainly possible. Tissue securement devices may be placed in different series, such as laterally across the stomach or in patterns, such as a zig-zag fashion to create an alteration of the volume, capacity, or function of the body cavity. Additionally, the location or distance between tissue securement devices can be varied as appropriate. In some embodiments, the distance between tissue securement devices may be very small. In such embodiments, the series of suture stitches may approximate and appose the tissue to form a partition that prevents or partially limits the passage of matter through the partition. Such partitions may prevent or partially limit the passage of food particles through the partition. Other embodiments may deploy tissue securement devices in a pattern that when the tissue is apposed together to form a partition, the partition prevents or partially limits the passage of liquids through the partition.

Figure 13:
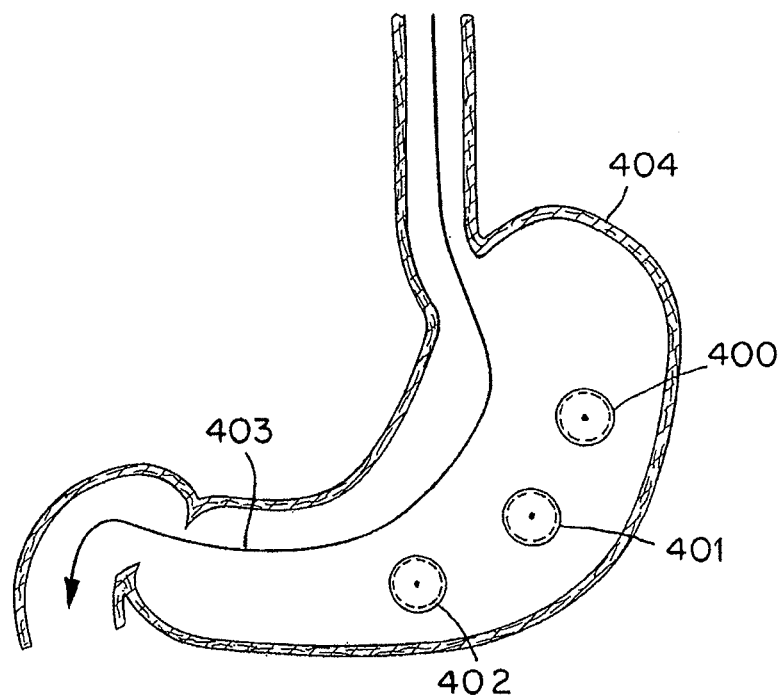
FIG. 13 through FIG. 15 are illustrations of different suture site configurations that are possible to alter the volume, capacity, or function of the stomach.
Figure 14:
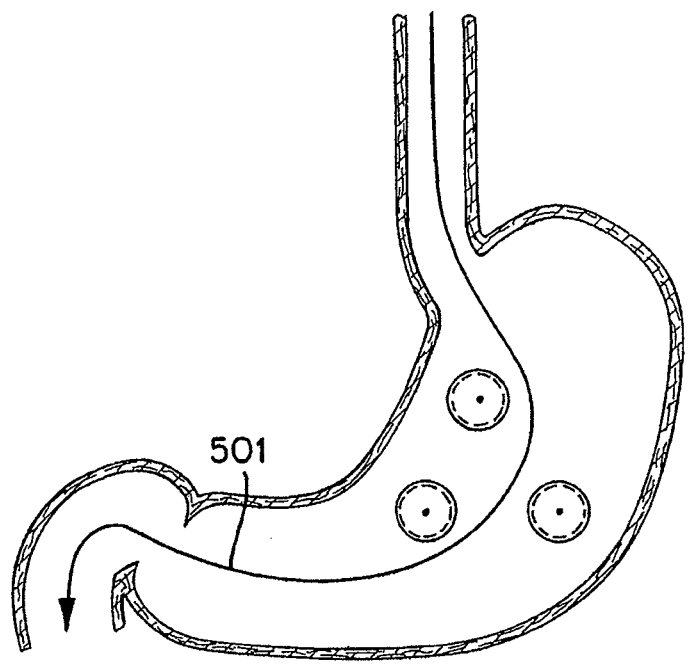
Figure 15:
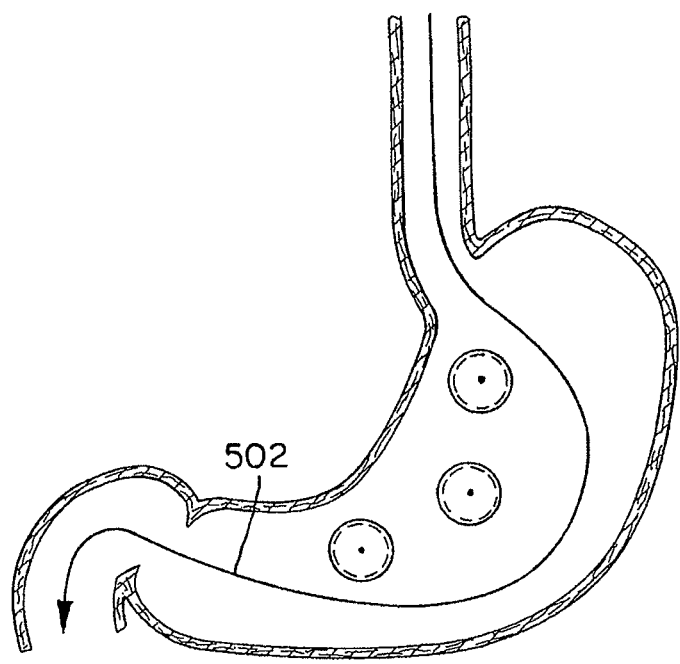
Figure 22:
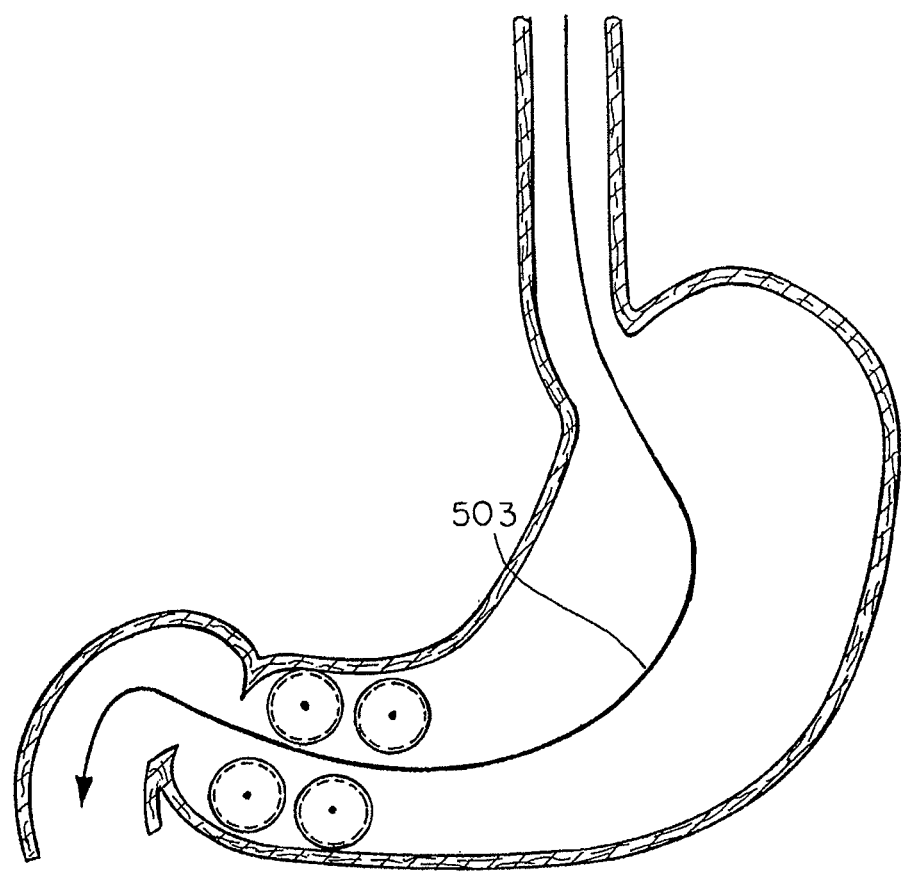
FIG. 22 is an illustration of tissue securement device sites proximal to the pylorus and antrum.

Further embodiments may include the deployment of at least one tissue securement device in a non-linear series. In such embodiments, the devices, such as a suture material, may be placed at a plurality of locations. The tissue securement devices may also be placed in clusters in locations or individually in locations within the cavity. In such embodiments, the tissue securement devices may approximate and appose the opposing walls together to alter the volume, capacity, or function of the stomach. FIG. 13 demonstrates one possible configuration. Three sites 400, 401, 402 are shown in FIG. 13 for illustrative purposes only, as a plurality of sites are possible. A single tissue securement device or a plurality of tissue securement devices may be placed at each site to approximate tissue. FIG. 14, FIG. 15 and FIG. 22 illustrate alternate embodiments of placing such sites. Again, a few tissue securement device sites are illustrated, but a plurality of tissue securement device sites may be used as appropriate. The arrows 403, 501, 502, 503 represent one possible pathway particles, such as stomach contents, may pass through the body cavity in the respective embodiments.

Embodiments of the present invention may include methods of promoting tissue adhesion between one or more portions of tissue to potentially reinforce tissue apposition sites. Some embodiments may utilize a tissue apposition device. In some embodiments, a plurality of tissue sites may be secured together by passing a tissue securement device, such as suture material, through each tissue site, tightening the securement device, and securing the tissue securement device. In embodiments that may use suture material, securing the tissue securement device may include, but are not limited to, a knot or a suture lock device. When the securement device is tightened, at least a portion of the tissue sites in which the securement device passes through will be approximated and may be placed in contact with some or all of the other tissue sites which are being approximated. The secured tissue securement device will maintain the tissue approximation. In some instances, however, the securement device may migrate or tear through the tissue over time, causing the tissue apposition to weaken or possibly fail. The amount of time the tissue securement device may maintain the tissue approximation varies on factors including, but not limited to, the individual patient, the depth the tissue securement device passes through the tissue, the physical properties of the tissue securement device, the consistency of the tissue, the tension on one or more tissue securement devices caused by the tightening one or more tissue securement devices, and the dynamic environment of the tissue and the body cavity. Therefore, multiple embodied methods are possible to strengthen the tissue apposition and reinforce the tissue approximation.

Embodiments of the present invention may include the use or presence of a fixation agent as part of a method to reinforce or strengthen a tissue approximation. This may include the placement of a fixation agent between a plurality of tissue sites, either before, during, or after the tissue approximation is secured. One such fixation agent may be, for example, a glue that is applied to at least one portion of the tissue sites that come into contact with other tissue sites within the tissue approximation. Fibrin glue is one example of a glue that may act as a fixation agent.

Figures 16A, 16B:
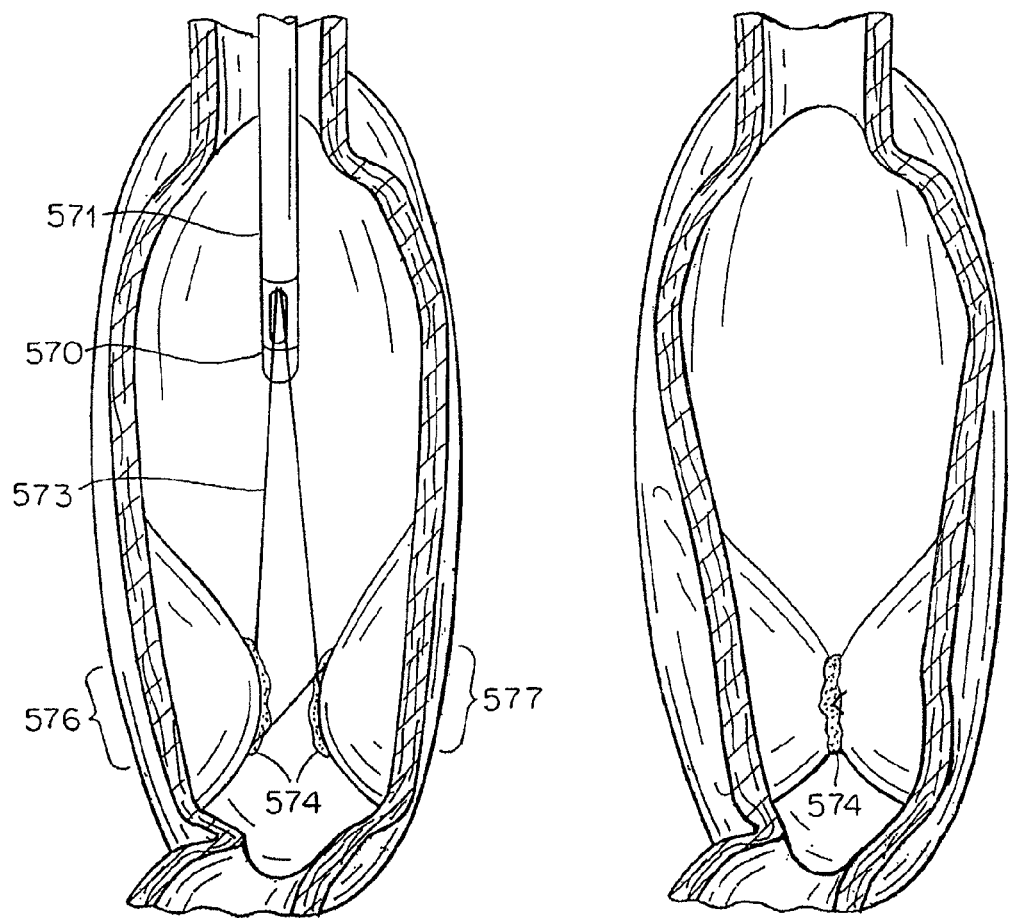
FIG. 16 is an illustration of the application of a glue or a fixation agent used in conjunction with a tissue apposition device to reinforce a tissue apposition.

FIG. 16 presents an illustration of an embodiment that used a glue as a fixation agent in conjunction with suturing. In FIG. 16, an interrupted suture stitch pattern is placed in a manner similar to FIG. 11, although many other stitch patterns are possible. After the tissue apposition device 570, which is mounted on a endoscope 571, has passed the suture material 573 through at least one tissue site, a fixation agent, such as a glue 574, may be applied to one or more of the at least one tissue sites. While FIG. 16A demonstrates only two tissue sites 576, 577 for illustrative purposes, the embodiments of the present invention may comprise a plurality of tissue sites.

Following the deployment of the fixation agent, the suture material is pulled tight and the tissue sites are approximated and at least a portion of the tissue site 576 comes into contact with at least a portion of other tissue site 577. The suture material may be secured by methods including, but not limited to, a knot or a suture lock, following which the suture material may be cut as appropriate, the results of which are illustrated in FIG. 16B. The two sites are now approximated and secured with the suture material. In the case where the fixation agent requires activation, the fixation agent may then be activated or begin the activation process that will promote tissue adhesion to reinforce the tissue apposition. When the fixation agent is embodied as a glue, the glue may cure and bind the portions of the tissue site 576 that come into contact with other portions of tissue site 577. It is, of course, understood that various aspects of the present invention will be apparent to those skilled in the art. For example, the glue may be applied to only a portion of tissue or all the tissue that comes into contact with the other tissue. Additionally, the glue may be applied to a portion or all of the tissue sites prior to the tissue apposition device passing the suture through one or more tissue sites or the glue may be applied after tissue apposition has occurred.

Certain embodiments of the present invention may use a fixation agent that promotes tissue adhesion to reinforce tissue apposition, where the fixation agent is adapted to promote tissue adhesion through tissue growing, healing, or scarring. A tissue adhesion may be formed between a plurality of tissue sites when one or more portions of the plurality of tissue sites grow tissue that connects and/or binds with one or more other portions of the plurality of tissue sites. Having one or more portions of one or more tissue sites fusing together with one or more other portions of one or more tissue sites through a growing, healing or scarring process may be referred to as tissue bridging. Embodiments of the present invention may comprise a fixation agent adapted to promote tissue bridging between two or more tissue portions, which may reinforce a tissue apposition and/or securement.

One embodiment of a fixation agent that promotes tissue adhesion may be one or more chemicals or substances that may act as a tissue growth factor. Examples of such chemicals or substances may include, but are not limited to, connective tissue growth factor (CTGF), vascular epithelial growth factor (VEGF), and tissue formation growth factor. The application of one or more chemicals or substances that may act as a tissue growth factor to one or more portions of tissue that are at least partially apposed together may accelerate, stimulate, or promote cellular growth between the one or more portions or tissue. This cellular growth may promote tissue bridging that may reinforce or strengthen a tissue apposition. Additionally, such chemicals or substances may accelerate, stimulate, or promote a healing or scarring process between the one or more portions of tissue that may be apposed.

One embodiment of a fixation agent that may facilitate tissue bridging between two or more portions of tissue is a body of biocompatible fabric. Such a biocompatible fabric may include a plurality of interstices which may be constructed or arranged to facilitate tissue infiltration and/or tissue bridging. The plurality of interstices may adapt the biocompatible fabric to allow tissue to infiltrate the fabric, which may act as a structure to promote new tissue development. A tissue apposition, where two or more portions of tissue are approximated and secured with a tissue apposition device, may comprise the biocompatible fabric with a plurality of interstices, whereby the plurality of interstices promote tissue bridging between two or more portions of tissue. The tissue bridging may reinforce the tissue apposition, wherein the reinforcement may increase the tissue apposition's resistance to being separated. The biocompatible fabric may be embodied by apparatuses including, but not limited to, a mesh of polypropylene monofilament or a mesh of PTFE monofilament.

Figures 17A, 17B:
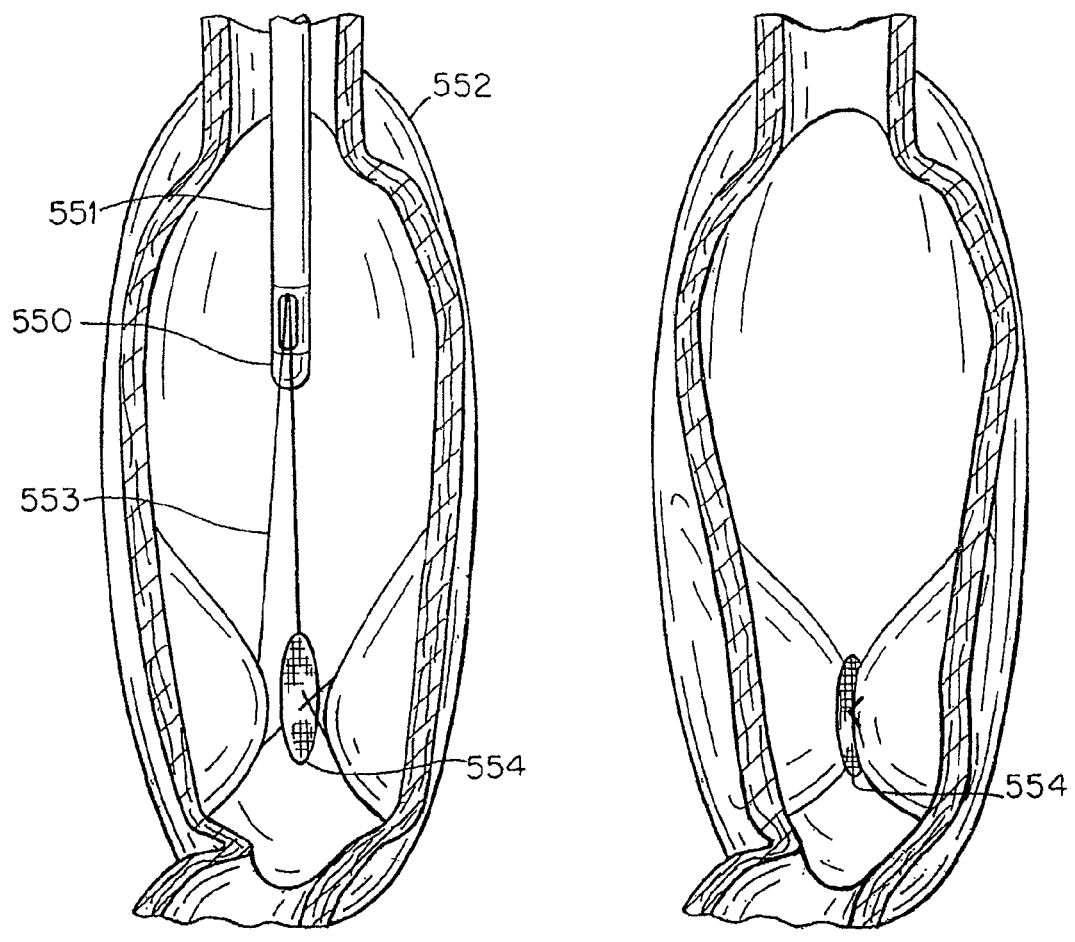
FIG. 17 is an illustration of the application of a biocompatible fabric to promote tissue bridging in conjunction with a tissue apposition device to reinforce a tissue apposition.

FIG. 17 illustrates one embodiment of the present invention that comprises a biocompatible fabric with a plurality of interstices secured between two or more portions of tissue within a tissue apposition. A tissue apposition device 550 is mounted on an endoscope 551, which can be navigated within the lumen of stomach 552. A tissue securement device, illustrated in FIG. 17 as a suture stitch, is placed in a manner similar to FIG. 11, although many other securement devices are possible. After the tissue apposition device 550 has passed the suture material 553 through a plurality of tissue sites, where the tissue sites may reside at least partially on opposing walls of the stomach from one another, the biocompatible fabric 554 may be fixated or secured into the tissue apposition. FIG. 17A demonstrates two portions of tissue comprised in the tissue apposition for illustrative purposes only, as a plurality of tissue sites are possible. After the biocompatible fabric 554 is incorporated into the tissue apposition, the suture material is pulled tight and the tissue sites are approximated. At least a portion of the tissue sites may come into contact with the biocompatible fabric. The suture material may be secured by methods described herein, following which the suture material may be cut as appropriate, resulting in what may be illustrated in FIG. 17B. Portions of tissue in contact or in the vicinity of the biocompatible fabric may undergo a tissue healing, growing, and/or scarring process and infiltrate the interstices of the biocompatible fabric. The tissue infiltration of the fabric may facilitate or undergo tissue bridging between two or more portions of tissue, which may create a tissue adhesion that will reinforce the tissue apposition.

One embodiment of a fixation agent that may facilitate tissue bridging between two or more portions of tissue is a body of resorbable material. By using a body of resorbable material, said body, when place within an in vivo environment, may be colonized by fibroblasts and revascularized. Examples of such a resorbable material may include, but is not limited to, animal or human collagen (especially porcine), animal or human intestinal sub-mucosal membrane, animal or human vesical sub-mucosal membrane, animal or human pericardium (especially bovine), portions of animal or human dermis, and/or a combination thereof. Said body of resorbable material may be either of human, animal, synthetic origin or a combination thereof. Such an embodiment may be placed between two or more portions of tissue, wherein the two or more portions of tissue may infiltrate or resorb one or more portion of the resorbable body into the tissue. The infiltration or incorporation of the fixation agent may promote tissue adhesion or tissue bridging between the two or more portions of tissue.

Additional embodiments of the present invention comprise methods and/or techniques to promote tissue adhesion to reinforce tissue apposition. Certain embodied methods may be, for example, promoting tissue bridging between one or more portions of tissue, whereby the tissue bridging is instigated as a result of a tissue healing process, a tissue growing process, or a tissue scarring process. By causing a tissue injury or tissue damage to one or more portions of tissue, the body's regenerative healing process may be enabled to undergo tissue bridging between the one or more portions of tissue.

There are many methods of damaging portions of tissue or causing tissue injury that may fall within the scope of various embodiments of the present invention. Examples of causing tissue damage include, but are not limited to, the application of electrical energy, the application of one or more chemical substances, the application of thermal ablation, the application of cryo ablation, and the application of mechanical abrasion. Additionally, examples of causing tissue damage may include the application of laser energy onto at least a portion of the tissue or the application of argon plasma onto at least a portion of the tissue.

Several embodiments may incorporate the application of electrical energy. Electrical energy may include radiofrequency energy (either monopolar or bipolar). The electrical energy, when applied to tissue, may ablate the mucosal and possibly the submucosal layers. Following the tissue ablation, a tissue healing or scarring process will begin to at least partially regenerate the damaged tissue. Such tissue healing or scarring processes may be adapted to promote tissue bridging.

Figure 18:
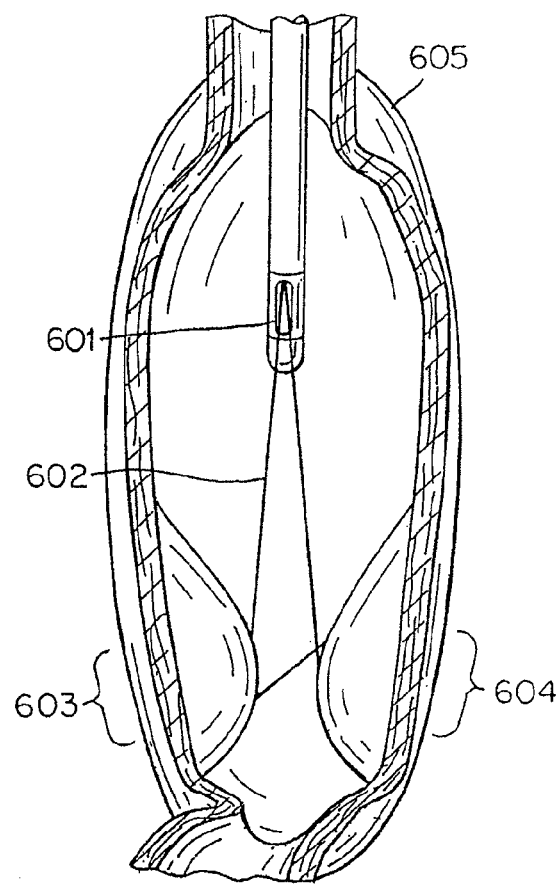
FIG. 18 is an illustration of the application of ablation to damage a portion of tissue to promote tissue bridging in conjunction with a tissue apposition device to reinforce a tissue apposition.
Figure 18:
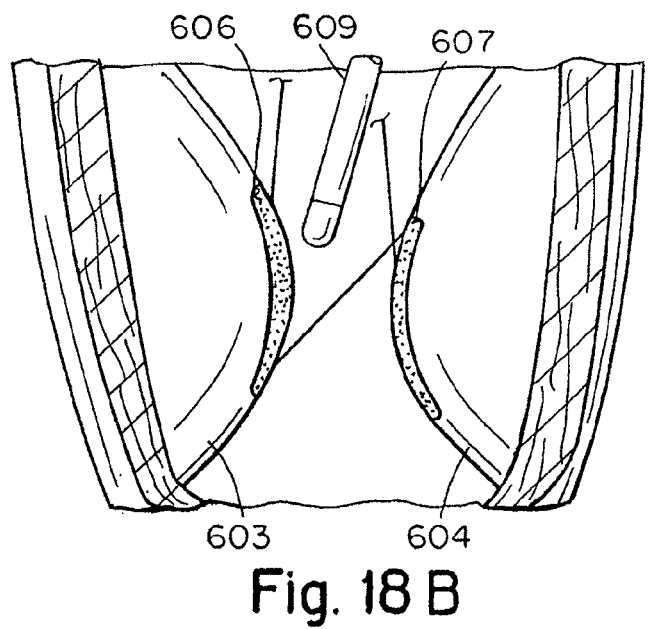
Figure 18:
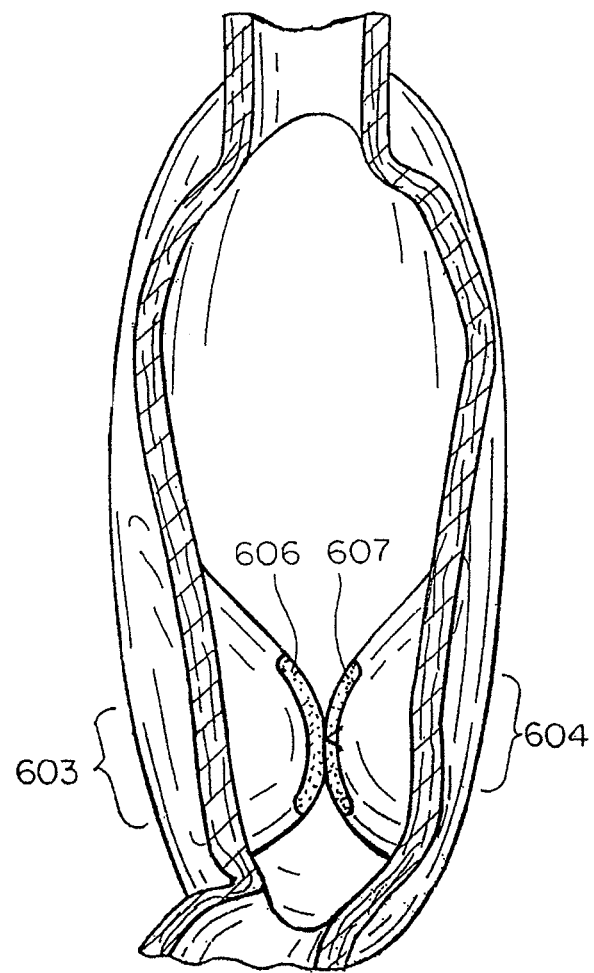

FIG. 18 demonstrates one possible embodiment that adapts electrical energy to ablate tissue, whereby the ablation promotes tissue bridging. Using a tissue apposition device 601 (as shown in FIG. 18(A)), a tissue securement device 602 (embodied in this illustration as suturing) is advanced through a first and second portion of tissue (603 and 604 respectively) in a manner that may be similar to that shown in FIG. 11. Tissue ablation may be accomplished through electrical energy. An electrocautery catheter or a similar device 609 is positioned within the body cavity 605 and is navigated into the vicinity of the first and second portions or tissue 603, 604, as illustrated in close up view in FIG. 18(B). By applying the electrical energy via the electrocautery catheter to the surface of the first and second portion of tissue, the mucosa and possibly the submucosal tissue may be ablated (606 and 607 respectively). The tissue damage or injury caused by the ablation may promote the healing or scarring process that may be adapted to promote the formation of tissue bridging. While the application of electrical energy is demonstrated, many other forms or combination of forms of ablation are adaptable to promote tissue bridging.

Following tissue ablation, the tissue securement device may be tightened and secured by methods described herein, as demonstrated in FIG. 18(C). The two portions of tissue 603, 604 have been apposed together with the ablated portions 606, 607 coming into at least partial contact with one another. Once the tissue apposition is secured and the ablated portions are at least partially in contact, the healing or scarring process may begin to grow the portions of tissue 603, 604 together. While two tissue portions are demonstrated in FIG. 18, embodiments of the present invention may comprise a plurality of tissue portions.

While FIG. 18 demonstrates an embodiment of damaging portions of tissue to promote tissue bridging, other embodiments are certainly possible. One such embodiment may comprise ablating the first and second portions of tissue prior to the tissue apposition device advancing a tissue securement device through the first or second portion of tissue. Another such embodiment comprises ablating the first and second portion of tissue after the tissue apposition means has been tightened and secured. Yet another embodiment comprises damaging the portions of tissue by a tissue ablation means incorporated into the tissue apposition device, whereby when the tissue is captured by the tissue apposition device, the tissue apposition device may ablate the collected tissue and cause tissue injury.

Alternate embodiments of the present invention are possible, wherein the application of ablation, such as electrical energy ablation, may be adapted to reinforce a tissue apposition. Electrical energy, or another appropriate form of ablation, may be applied to the tissue in order to promote a healing, growing, or scarring process. The application of ablation may be applied to one or more portions of tissue, whereby the ablation is conducted from the ablation source to the one or more portions of tissue via elements including, but not limited to, one or more tissue securement devices and one or more fixation agents. The one or more tissue securement devices or the one or more fixation agents may be comprised of a conductive material or have a coating of conductive material at least partially incorporated on or within the one or more tissue securement devices or one or more fixation agents. In such embodiments, when the ablation is conducted through a tissue securement device or fixation agent, the ablation may be discharged or applied to at least a portion of tissue that may be in contact with the tissue securement device or fixation agent. As a result, tissue damage may be applied to the at least a portion of tissue.

Figure 19A:
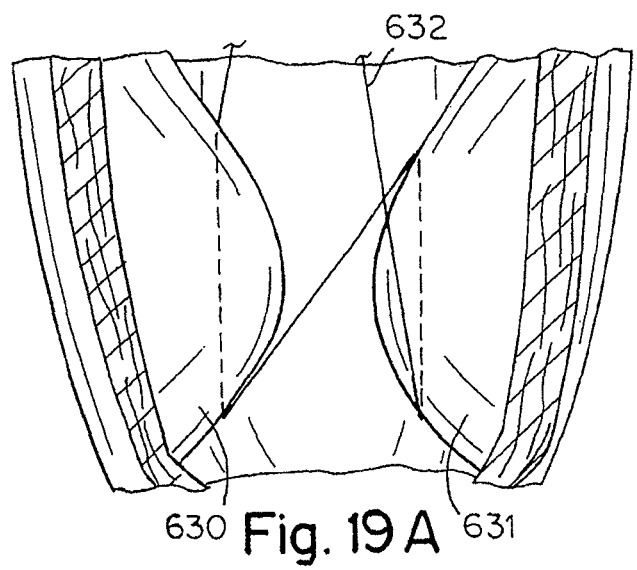
FIG. 19 is an illustration of the application of ablation to damage one or more portions of tissue, wherein the ablation is transmitted through a tissue securement device.
Figure 19B:
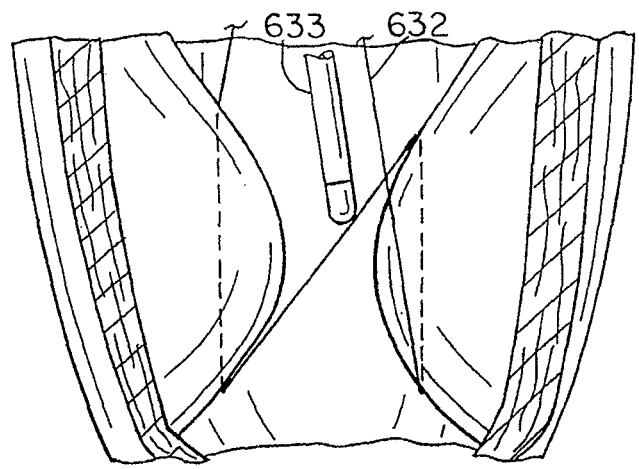
Figure 19C:
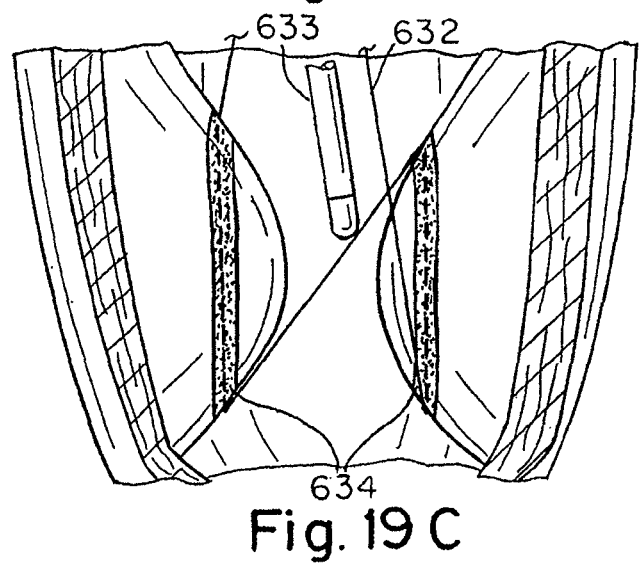

FIG. 19 illustrates one example of conducting ablation through a tissue securement device to cause tissue damage. In this example, the tissue securement device is embodied by suture material 632. Said suture material may be comprised of a material that is conductive of the ablation or coated with a material that is conductive of the ablation. The suture material 632, as demonstrated in FIG. 19A, is or has been advanced through two or more portions of tissue 630, 631 in a manner similar to methods and embodiments described herein. A source of ablation 633, such as an electrocautery catheter that may be used for the application of electrical energy, is positioned within the body cavity and may be placed in contact with the tissue securement device, shown in FIG. 19B. With the source of ablation at least partially in contact with the tissue securement device, the ablation may be applied. The ablation may be conducted through the tissue securement device and applied to one or more portions of tissue that are in contact with the tissue securement device. The application of ablation to one or more portions of tissue may cause tissue damage 634 to the tissue, which may promote a healing or scarring process. When new tissue or scar tissue has grown/formed in response to the tissue damage, the tissue may be tougher and/or more fibrous and therefore have a higher resistance to the tissue securement device pulling or tearing out of the one or more portions of tissue. By strengthening the resistance against tissue securement device migration out of the tissue, the embodiment reinforces the tissue apposition.

FIG. 20 demonstrates a further embodiment. In this embodiment, ablation may be conducted through a fixation agent to cause tissue damage. In this example, where the fixation agent may be embodied as a body of biocompatible fabric, said fixation agent may be comprised of a material that is conductive of the ablation or the fixation agent may be coated with a material that is conductive of the ablation.

Figure 20A:
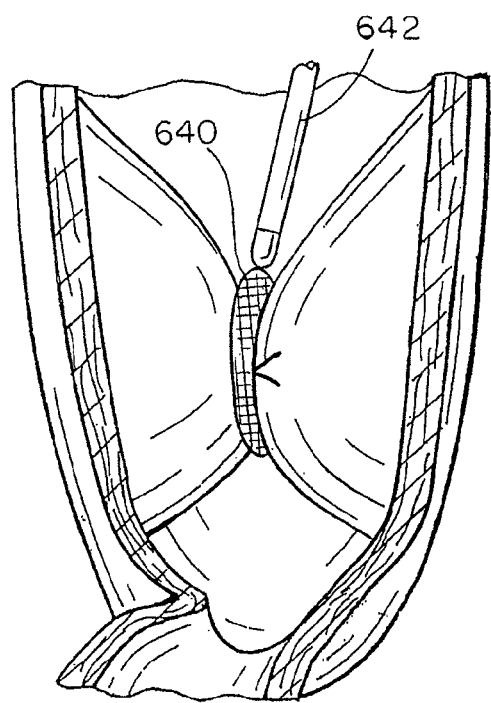
FIG. 20 is an illustration of the application of ablation to damage one or more portions of tissue, wherein the ablation is transmitted through a fixation agent.
Figure 20B:
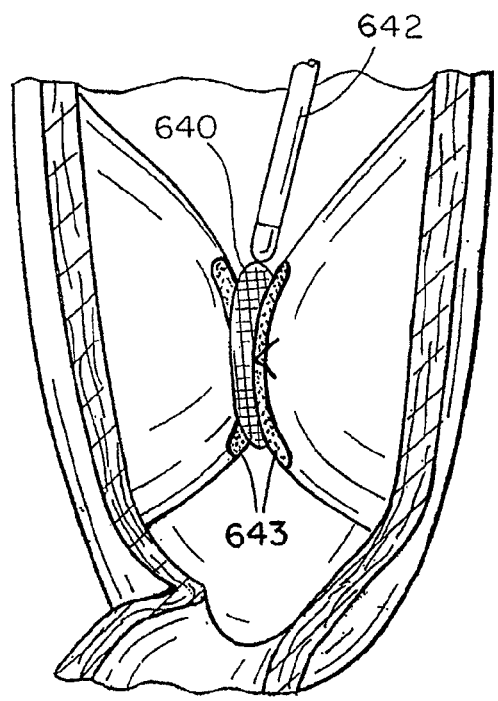

A fixation agent is placed and secured within a tissue apposition in a manner similar to methods and embodiments described herein. With the fixation agent in place, as shown in FIG. 20A, an ablation source 642 is positioned within the body cavity and is placed at least partially in contact with the fixation agent 640. Ablation may then be applied by the ablation source and the ablation may be conducted through the fixation agent, whereby the ablation is applied to one or more portions of tissue in contact with the fixation agent. This is illustrated in FIG. 20B. The application of ablation may cause tissue damage 643 to the one or more portions of tissue, thereby promoting a growing scarring or healing process response. New tissue growth may infiltrate the fixation agent and fuse with one or more portions of other tissue. Tissue bridging may be formed, thereby reinforcing the tissue apposition and increasing its resistance to being separated.

Further embodiments of the present invention comprise the use of different forms or combinations of ablation. The application of one or more chemical substances, including but not limited to sodium morrhuate, to a portion of tissue may cause tissue damage and ablation. The chemical substance may be applied topically or injected below the surface of the portion of tissue. By performing tissue ablation with one or more chemical substances to one or more portions of tissue, said portions of tissue may be approximated and apposed with a tissue apposition device, whereby at least a portion of the ablated tissue is placed in contact with at least a portion of another ablated portion of tissue, such that tissue bridging may form. Such tissue bridging may reinforce the tissue apposition.

The use of mechanical means or mechanical abrasion may also be used to cause ablation in one or more portions of tissue. Examples of mechanical means or mechanical abrasion may include, but are not limited to, performing mucosal resection, or abrading the tissue with elements such as a rough texture member or with a brush-like device such as a cytology brush. The one or more portions of tissue may be abraded by one or more mechanical means and may be approximated and apposed with a tissue apposition device. When the healing or scarring process begins, the mechanically ablated portions of tissue may undergo tissue bridging to reinforce the tissue apposition.

Embodiments of the present invention may also use one of thermal ablation and cryo ablation. By exposing one or more portions of tissue to an extreme temperature, the mucosa and possibly the submucosa may be ablated. The one or more portions of tissue may be approximated and apposed within a tissue apposition, whereby the healing or scarring process may promote tissue bridging to reinforce the tissue apposition.

In certain embodiments of the present invention, a tissue apposition device, comprising at least one tissue securement device, may be positioned within the stomach to approximate and secure two or more portions of tissue together into a tissue apposition. The approximation and securing of two or more portions of tissue may be selected from methods described herein. The position of the portions of tissue comprised within the tissue apposition may be chosen from a plurality of sites within the stomach or organ system substantially adjacent to the stomach. Sites may include, but are not limited to, the stomach's fundus, cardia, body, antrum, and pylorus. The placement of one or more tissue appositions may inhibit or present forces that may oppose the forces exerted by the mechanical contractions of the stomach. The forces may be applied in manners including, but not limited to, longitudinal forces 651 and circumferential forces 652 within the stomach 650, both illustrated in FIG. 21. By opposing the forces exerted by the stomach, one or more of the stomach's functions may speed up or the function may slow down. For example, one or more tissue appositions may inhibit or slow down the stomach's peristalsis. Additionally, for example, one or more tissue appositions may inhibit the contractions of the antrum and/or pylorus, whereby the inhibition of the contractions cause the stomach's content to remain in the stomach for a longer period of time.

An embodiment of placing tissue appositions near the pylorus as illustrated in FIG. 22, whereby the placing tissue apposition may lengthen or elongate the pylorus or pylorus channel. By lengthening or elongating the pylorus or pylorus channel, the size of the stomach contents allowed to pass through the stomach and into the small intestine may be substantially reduced. In such cases, the stomach contents are held in the stomach for a longer period of time (delaying gastric emptying and possibly promoting satiety), whereby the stomach content may be further broken down. Lengthening or elongating the pylorus or pylorus channel in this manner may also shorten the antrum, which contributes to a portion of the grinding and/or propelling of stomach contents towards the pylorus. Shortening the antrum may reduce the grinding and propulsion forces in the stomach to further delay gastric emptying.

One function that may be altered as a result of one or more tissue appositions applying one or more forces to oppose one or more forces exerted by the stomach's mechanical contractions may include gastric transport. Particles of food and matter that enter the stomach (collectively referred to as stomach contents) are at least in part, mixed and transported through the stomach via stomach muscle contractions. Transportation may be accomplished by peristalsis or a peristalsis-like motion. By placing one or more tissue appositions within the stomach that apply one or more forces to oppose one or more forces exerted by the stomach's mechanical contractions, the gastric transport of stomach content may be altered.

Gastric emptying rate may be defined as the amount of time the stomach takes to transport stomach contents from the stomach into the intestines. By applying one or more forces that may oppose one or more forces exerted by the mechanical contractions of the stomach, the gastric emptying rate may increase—the stomach content may remain in the stomach longer. By keeping stomach contents within the stomach, the patient may maintain a sense of fullness and/or satiety longer and therefore potentially reduce the patient's food intake. The reduction in food intake may lead to weight loss.

Further embodiments of the invention may place one or more tissue apposition devices comprising one or more tissue securement devices, wherein the tissue apposition or method of placing the tissue apposition or the devices used in the creation of the tissue apposition alter the production of gastric secretions from portions of gastric secretion producing tissue. Said gastric secretion producing tissue may be comprised within the tissue apposition or in the substantial vicinity of the tissue apposition. Gastric secretions may include, but are not limited to hormones, stomach acid, and digestive enzymes.

Figure 21:
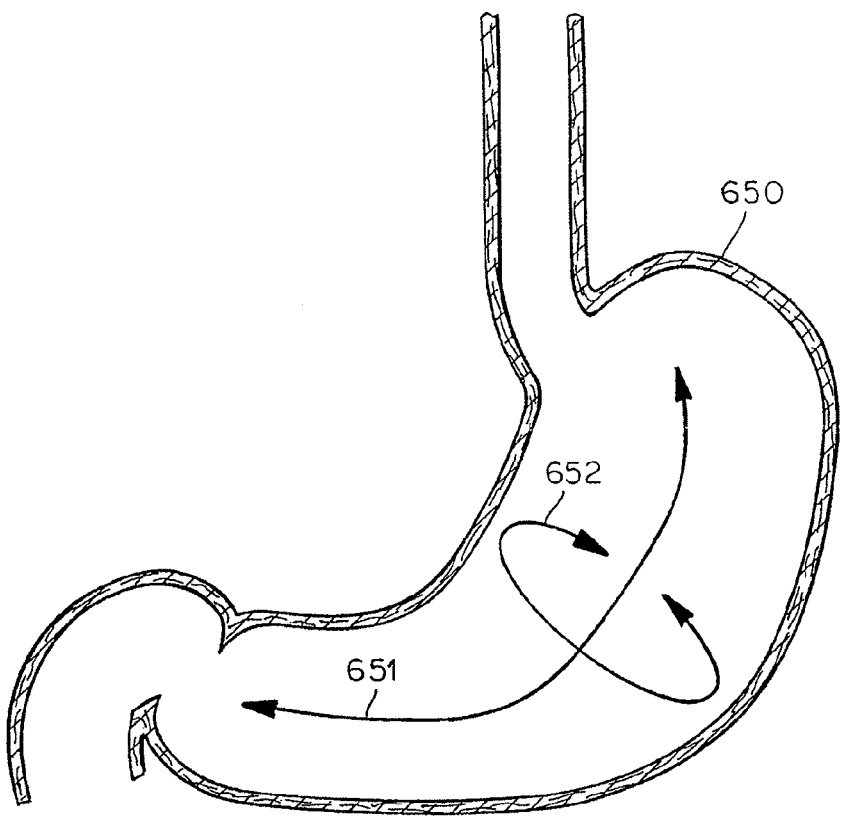
FIG. 21 is an illustration demonstrating longitudinal and circumferential directionality.

Embodiments of the present invention may place one or more tissue appositions within the stomach, wherein when the tissue securement device is tightened and possibly secured, the tightening exerts one or more forces on one or more portions of gastric secretion producing tissue. The one or more forces may be, for example longitudinal or circumferential in direction, as illustrated in FIG. 21. The one or more forces may alter the function of the one or more portions of gastric secretion producing tissue and alter the production of said gastric secretion. Such alterations may include the increase, decrease or cessation of gastric secretion production. Examples of forces exerted by a tissue securement device on a portion of gastric secretion producing tissue are illustrated in FIG. 23.

In FIG. 23A, a tissue securement device 701 is placed within a stomach 700, whereby the placement of the tissue securement device is such that a tissue apposition 702 is formed. As a result of the tissue apposition, tissue comprised within the tissue apposition or in the substantial vicinity of the tissue apposition 704 may be subjected to one or more forces as a result of the tissue apposition. The one or more forces may cause the gastric secretion producing tissue, such as hormone producing tissue, and/or the cells that make up the tissue to stretch 703, as indicated in the enlarged fragmentary view of FIG. 23A1, whereby the stretching alters the gastric secretion production. An alternate example is illustrated in FIG. 23B. Again, a tissue securement device 705 is placed within a stomach 708 and a tissue apposition 706 is formed. Gastric secretion producing tissue comprised within the tissue apposition or in the substantial vicinity of the tissue apposition 709 may be subjected to one or more forces exerted by the tissue apposition. Said forces may compress 707 the gastric secretion producing tissue and/or the cells that make up the tissue, as indicated in the enlarged fragmentary view of FIG. 23B1, whereby the compression alters gastric secretion production.

Other embodiments exist, wherein the placing or advancing the tissue securement device through a portion of tissue may cause an alteration in the production of gastric secretion within gastric secretion producing tissue. Said alteration may be at least partially resulting from tissue damage caused by the placing or advancing of the tissue securement device or the presence of the securement device within the tissue.

By altering the hormone production of at least a portion of hormone producing tissue, the quantity of said hormone may increase or decrease within the patient's body. Embodiments that alter the hormone production of hormones that at least partially contribute to the patient's sensation of appetite or satiety may cause the patient to alter the amount of food that is eaten or taken in. This alteration in consumed food may cause the patient to lose weight as a result. Examples of such hormones that may at least partially contribute to the patient's sensation of appetite or satiety include, but are not limited to ghrelin, leptin, and adiponectin.

Embodiments of the present invention may alter the production of gastric secretions that at least partially contribute to the patient's ability to break down food particles within the stomach. Additionally, embodiments may alter the release of gastric secretions into the stomach, whereby causing delays in the gastric emptying rate of the patient and potentially promoting a feeling of satiety. Such a feeling of satiety may alter the amount of food that is eaten or taken in by the patient. This alteration in consumed food may cause the patient to lose weight as a result. Examples of such gastric secretions that may at least partially contribute to the patient's ability to break down particles in the stomach includes, but is not limited to gastric acid and digestive enzymes.

Certain embodiments of the present invention may inhibit the production of gastric produced hormones, such as ghrelin. In such embodiments, the advancement of the tissue securement device or the tightening of the tissue securement device may cause changes or promote inhibiting forces on endocrine cells within the stomach tissue. The changes or inhibiting forces on endocrine cells may include compression forces on the cells, stretching forces on the cells, disruption of intracellular space chemistry, disruption of ion transport in surrounding cells, or disruption of protein synthesis.

An embodiment of the present invention may comprise a tissue apposition device that may be positioned within the stomach cavity at the vicinity of the gastric fundus. Using one or more tissue securement devices, a tissue apposition may be created that may include at least a portion of the tissue in the vicinity of the gastric fundus. Given that endocrine cells residing in the vicinity of the gastric fundus are a main sourced of the production of hormones such as ghrelin, the tissue apposition may stretch, compress, or otherwise alter the cellular environment which may negatively affect the protein synthesis of hormones such as ghrelin. As a result, the hormone production may be altered. The altered hormone production may cause a change in the satiety the patient experiences, thereby causing the individual to eat less food. The reduction in food intake may cause weight loss in the patient.

Methods described herein may comprise the use of one or more tissue apposition devices selected from a plurality of potential tissue apposition devices to appose and/or join internal tissue together. Certain embodiments of the present invention may include one or more tissue apposition devices that may comprise of an energy emitting member or component, wherein the energy emitting member or component may be adapted to apply energy to tissue in order to promote a tissue healing process, a tissue growing process, or a tissue scarring process. The energy may be applied to the tissue to produce an injury to the tissue. Certain embodiments may be, for example, adapted to promote tissue adhesion between one or more portions of tissue to reinforce one or more tissue appositions. Certain embodiments may promote tissue bridging between one or more portions of tissue, whereby the tissue bridging is instigated as a result of a tissue healing process, a tissue growing process, or a tissue scarring process. Energy that may be emitted from an energy emitting member may include, but is not limited to, electrical energy, chemical energy, or thermal energy. Electrical energy may further comprise radiofrequency energy.

In certain embodiments of the invention, one or more energy emitting members may be operably coupled to one or more tissue apposition devices or operably couple to one or more tissue securement devices. Embodiments may further comprise a member or component for collecting tissue. The one or more energy emitting members may be adapted to apply energy to tissue that many be collected by the tissue apposition device in order to promote a tissue healing process, a tissue growing process, or a tissue scarring process—processes which may reinforce a tissue apposition. Furthermore, energy may be applied to tissue collected by a tissue apposition device to produce an injury to the tissue.

Figure 24A:
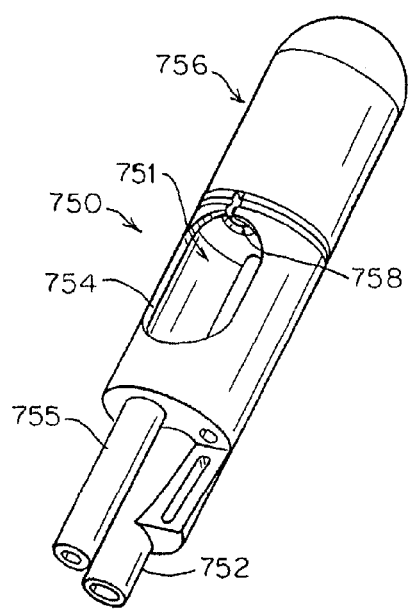
FIG. 24 is an isometric view of a tissue apposition device comprising a vacuum cavity.
Figure 24B:
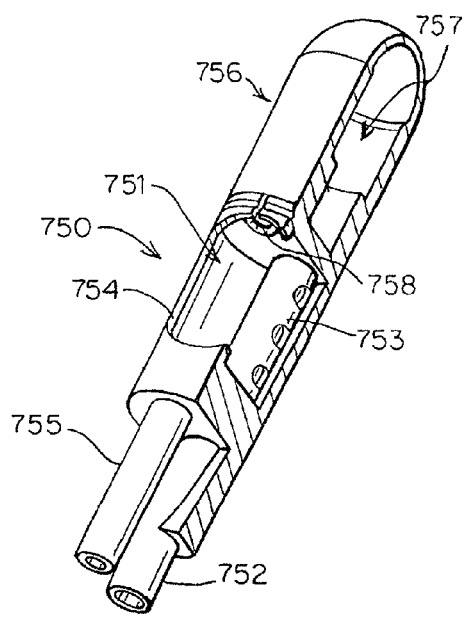

FIG. 24 illustrates an embodiment of a tissue apposition device (750) that may have one or more energy emitting members operably coupled to the embodied device. FIG. 24A illustrates an isometric view of an embodied tissue apposition device. FIG. 24B illustrates a three dimensional view of the embodiment, with a planar cut-away in order to visualize the internal features/components of the device. The tissue apposition device (750) comprises a cavity (751) within the device. The cavity may be adjacent to and in communication with a vacuum channel (752). The cavity and the vacuum channel may be in communication with one another via a vacuum channel interface (753). The vacuum channel interface may be adapted to selectively allow the passes of gases, liquids, and solids between the cavity and the vacuum channel. In the illustrated example, the vacuum channel interface is embodied by a series of perforations in the vacuum channel, wherein the size of the perforations may be selected to allow free passage of gas and liquid between the cavity and the vacuum channel, while restricting the passage of solids which are greater in dimension than the dimension of the perforations. In this embodiment, when vacuum is applied to the vacuum channel, tissue that is in proximity of the cavity opening (754) will be drawn into or collected into the cavity.

Some embodiments of the present invention may further comprise one or more tissue securement devices. In FIG. 24, the illustrated embodiment may comprise suture as a tissue securement device. The suture may be coupled to a needle by a suture tag. The suture tag is releasably coupled to the needle in order to facilitate suturing. 755 may represent a suturing channel within the described embodiment. The needle, suture, and/or suture tag (not shown in FIG. 24) may be slidably positioned within the suturing channel (755). When tissue is collected into the cavity, the needle, suture, and/or suture tag may be advanced through the suture channel into the cavity (751). The needle, suture, and/or suture tag may be advanced through at least a portion of the tissue collected within the cavity and may be further advanced into a distal portion of the embodied tissue apposition device (756). The distal portion of the embodied tissue apposition device (756) may comprise a chamber (757) and a chamber interface (758). The chamber (757) may be in communication with the cavity (751) via the chamber interface (758). When the needle is advanced into the chamber (757), the suture tag may be released from the needle and deposited into the chamber (757). The needle may be retracted back into the suturing channel, leaving the suture within the tissue. FIG. 24 represents one possible embodiment of a tissue apposition device wherein one or more energy emitting member or component may be operably coupled to the tissue apposition device, as illustrated in FIG. 25 and FIG. 26.

Embodiments of an energy emitting member or component may include elements that emit electrical energy or radiofrequency energy. Energy emitting members or mechanisms may further comprise radio frequency electrocautery electrodes. One possible embodiment of an electrical energy emitting member or mechanism is illustrated in FIG. 25, where the electrical energy emitting member or mechanism is embodied as a flexible electrical circuit. The substrate of the flexible electrical circuit may be chosen such that the circuit is malleable and/or deformable. As such, the flexible electrical circuit may be formed into a particular shape as it is operably coupled to a tissue apposition device or a tissue securement device. FIGS. 25A&B illustrate the embodied energy emitting member in a flat shape. FIG. 25C illustrates the embodied energy emitting member in a rolled shape. The shape illustrated in FIG. 25C may be the preferable shape for operably coupling the embodied energy emitting member to a tissue apposition device.

Figure 25:
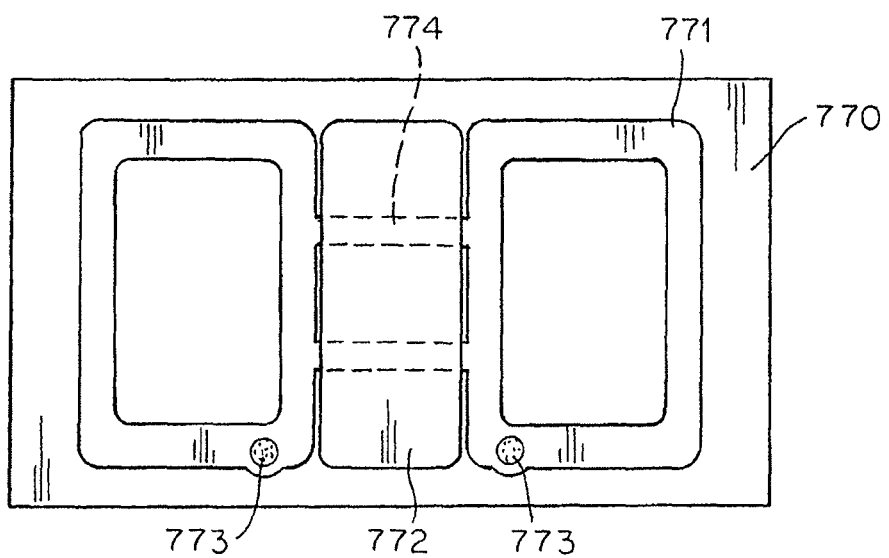
FIG. 25 are illustrations of a flexible circuit design.
Figure 25B:
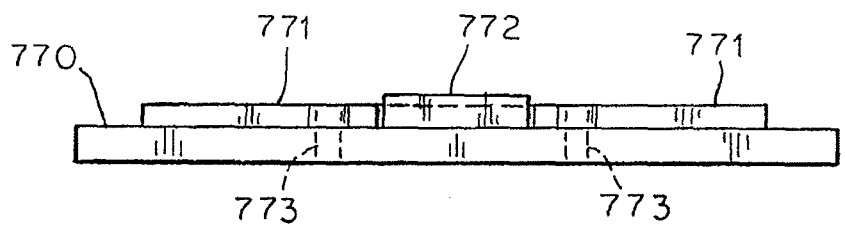
Figure 25C:
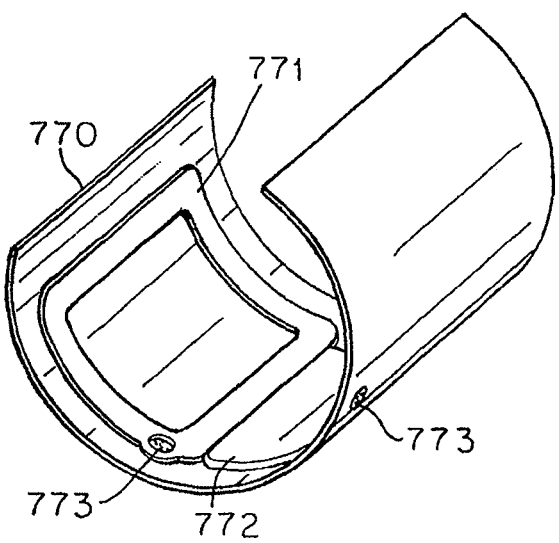
Figure 26:
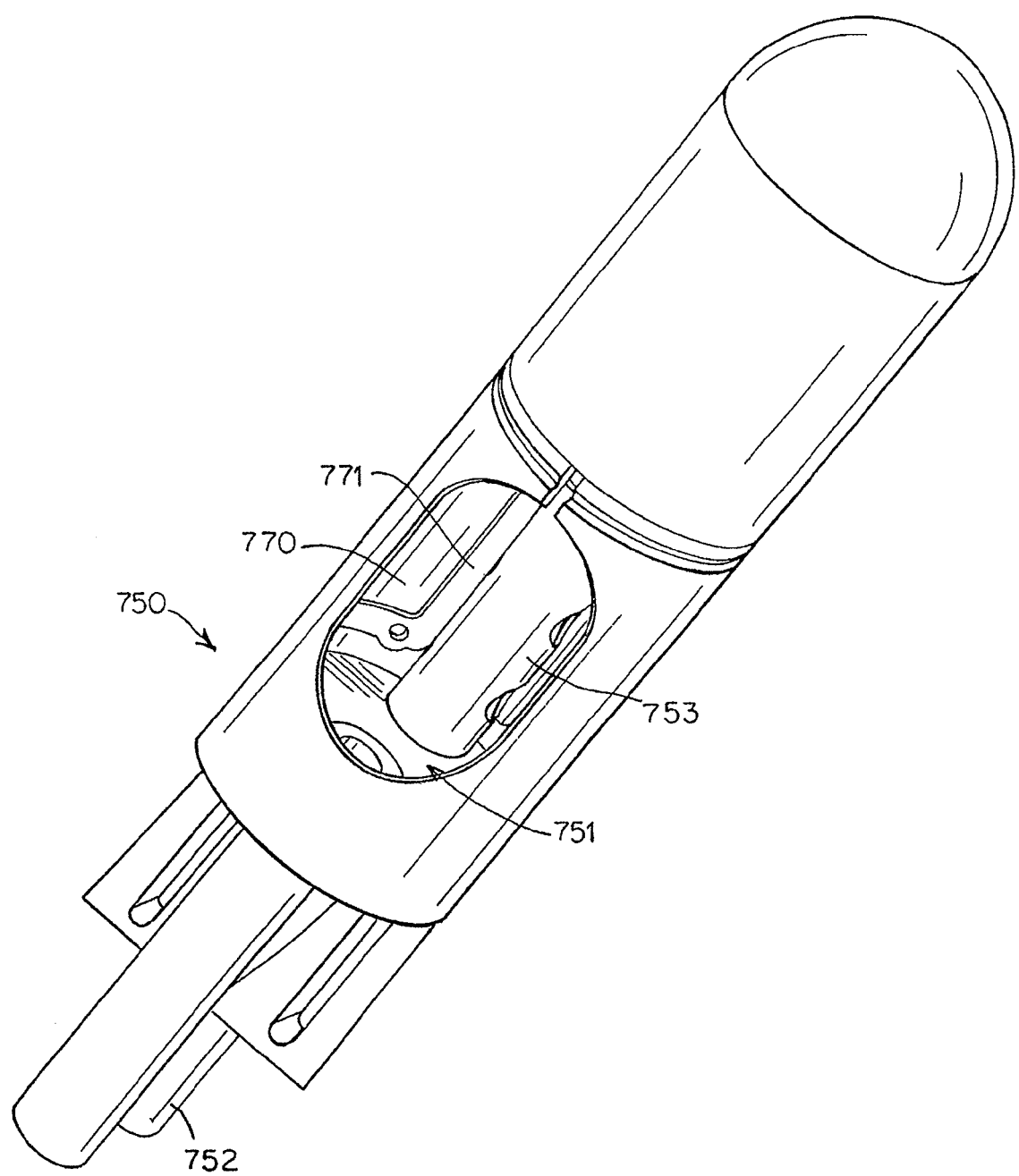
FIG. 26 is an isometric view of a flexible circuit disposed within a vacuum cavity of a tissue apposition device.

The flexible energy emitting member or component embodied in FIG. 25 may comprise one or more layers of material. FIG. 25A, which may represent a top view, and FIG. 25B, which may represent a side view, illustrate possible layers. A non-conductive layer may form the base layer (770). The base layer (770) may comprise of a flexible non-conductive or dielectric material. This material may preferably be selected from a group comprising polyimide and Teflon. Polyimide has a very high dielectric strength (7,700 volts/mil), which make it a preferable material. Teflon, which has a dielectric strength of 6,500 volts/mill, may also be used. The dielectric strength of the non-conductive layer allows the layer to electrically insulate the embodied energy emitting member.

Layered on top of the base layer (770) may be a middle layer (771), which may preferably comprise a conductive material. A preferred conductive material may be copper. Other possible materials may also include gold or stainless steel. The middle layer (771) may be pattern in multiple configurations. The middle layer (771) may comprise conductive traces that may be bonded to the base layer via an adhesive such as an acrylic adhesive. A top layer (772) may be optionally layered on top of the middle layer (771). The top layer (772) preferably comprise a non-conductive material and may be the same non-conductive material as the base layer (770). Preferable materials for the top layer may be polyimide or Teflon.

The top layer (772) and/or the base layer (770) may be adapted to cover or insulate portions of the middle layer (771) that may be sandwiched between the top layer (772) and base layer (770). Portions of the middle layer which are insulated by at least a portion of the top layer and at least a portion of the base layer (770) is illustrated in FIG. 25 as (774). The top layer (772) and/or base layer (770) may also be adapted to expose portions of the middle layer (771). The exposed portions of the conductive middle layer may act as one or more electrodes or a portion of the embodied energy emitting member that emits energy to tissue in contact or in close proximity with the exposed positions of the middle layer. The middle layer (771) may be patterned on a symmetrical presentation of two conductive rectangular frames, as illustrated in FIG. 25, but a plurality of other configurations are possible.

In embodiments of the present invention wherein the middle layer comprises a copper material, the weight of the copper traced may be approximated 0.5 oz, but may also range up to 2.0 oz or higher as needed.

Embodiments of an energy emitting member comprising a flexible layered circuit may have one or more power channel interfaces 773, as illustrated in FIG. 25. The one or more power channel interfaces may be adapted to connect to a power channel, which may provide electrical energy to the embodied energy emitting element. In the embodiment shown in FIG. 25, the power channel interface comprises one or more holes that pass through one or more of the circuit's layers. This may allow for a power channel to be coupled to the power channel interface. As such, the power channel may be in electrical communication with the conductive layer via the power channel interface. Examples of embodiments of a power channel included, but are not limited to, conductive leads, conductive wires, or conductive cables.

In embodiments of the present invention comprising of a flexible circuit, as illustrated in FIG. 25, the flexible circuit may be formed into a plurality of shapes; A preferable shape may be formed, which may facilitate an operable coupling with a tissue apposition device or a tissue securement device. For example, an embodiments of flexible circuit may be rolled up, as shown in FIG. 25C, which may facilitate the coupling within a tissue apposition device embodiment. In tissue apposition device embodiments that comprise a cavity, like the cavity (751) illustrated in FIG. 24, the flexible circuit may be coupled to the tissue apposition device within the cavity.

Certain embodiments of the energy emitting member may conform and/or be coupled to walls of the cavity. An embodiment of an energy emitting member being coupled to a tissue apposition device, wherein the tissue apposition device comprises a cavity and the energy emitting member is coupled to at least a portion of the walls of a cavity is illustrated in FIG. 26. In FIG. 26, the tissue apposition device (750) may comprise a cavity (751). Within the cavity, an energy emitting member may be coupled to the wall of the cavity. As configured, the conductive layer (771), may be exposed to the space within the capsule. The non-conductive base layer (770) may insulate the conductive layer (771) from the body or wall of the tissue apposition device (750). Furthermore, the vacuum channel (752) and vacuum channel interface (753) may be insulated from the conductive layer (771), by one or more non-conductive layers, such as the top layer (772).

In embodiments such as those described in FIG. 24-FIG. 26, the energy emitting member may be embodied as a layered flexible circuit comprising one or more conductive layers and one or more non-conductive layers. The one or more conductive layers may be sandwiched between one or more non-conductive layers, which may insulate the one or more conductive layers from the body of the tissue apposition device. This insulating feature in preferred embodiments allows the device and tissue to be protected against unwanted emission of energy.

Certain embodiments of the present invention may comprise one or more energy emitting members, wherein an injury may be caused to tissue in contact or in close proximity to the energy emitting members. Examples of energy emitting members include, but are not limited to, an electrode or a conductive layer of a flexible circuit. In embodiments wherein the injury caused to tissue is accomplished by electrical energy or radiofrequency energy, the energy emitted by the energy emitting member may be provided or facilitated by an electrosurgery generator. The generator may be in electrical communication with the energy emitting member by a power channel. The energy provided or facilitated by the electrosurgery generator may preferably be a very high frequency, intermittent AC electrical waveform, suitable for coagulation. The delivery of the energy to the tissue may be adapted in a monopolar or bipolar configuration.

As energy is delivered to the tissue, electrosurgical desiccation may occur. In preferable embodiments, the energy is adapted such that the electrosurgical desiccation is not in a cutting mode. An interrupted waveform spread over a larger surface area may produce less heat and, instead of tissue vaporization, the waveform may produce a coagulum. The variable that preferably determined if a waveform (energy) may cut tissue or if the waveform (energy) may produce a coagulum may be the rate of heat that is produced at the site. High heat may cause vaporization, while lower heat may create a coagulum. A preferable embodiment comprises low heat produced with an intermittent waveform to produce a coagulum.

Figure 27:
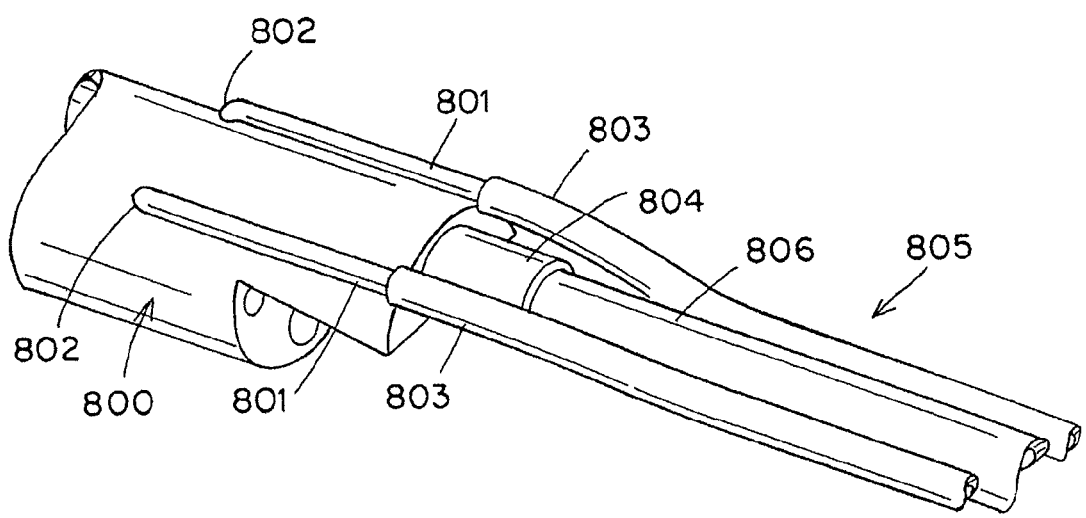
FIG. 27 is an illustration of power channels coupled with a tissue apposition device.

FIG. 27 demonstrates one embodiment where one or more power channels may be adapted to a tissue apposition device (800) in order to provide power and/or energy to one or more energy emitting members or components. In the illustrated embodiment, the tissue apposition device (800) may comprise a tissue suction cavity wherein the tissue suction cavity further comprises one or more energy emitting members or components. (In FIG. 27, neither the tissue suction cavity or the one or more energy emitting members or components are illustrated.)

One or more power channels (801) may be adapted to the tissue apposition device (800) wherein the power channels are in communication with the one or more energy emitting members or components (preferably via electrical communication). In the illustrated embodiment, the communication between the one or more power channels and the one or more energy emitting members or components may be facilitated by one or more break-throughs (802) in the body wall of the tissue apposition device (800). The power channels are preferably electrically insulated from all the components of the tissue apposition device (800) with the exception of the one or more energy emitting members or components. This may be accomplished by insulating the one or more power channels and the interface between the one or more power channels and the one or more energy emitting members or components with a barrier comprising a material with a high dielectric strength. Such a material with a high dielectric strength may be polyimide or Teflon, for example.

The one or more power channels (801) as illustrated in the embodiment shown in FIG. 27 may be adapted to traverse the distance between the tissue apposition device (800) and the means of providing or facilitating power or energy, such as an electrosurgery generator (not shown in FIG. 27).

In preferred embodiments, the tissue apposition device (800) may further comprise a vacuum channel (804) and a vacuum cavity (not shown in FIG. 27), wherein the vacuum channel may be in communication with the vacuum cavity. The one or more power channels (801) may be in close proximity with the vacuum channel (804). Furthermore, the one or more power channels (801) and the vacuum channel (804) may traverse at least a portion of the distance from the tissue apposition device (800) to their respective sources (which may include an electrosurgery generator or a vacuum source) via a similar pathway. This pathway may be embodied as a multi-lumen pathway (805), wherein the vacuum channel may be disposed within one or more of the multi-lumen pathway's lumens and the one or more power channels may be disposed within the same one or more of the multi-lumen pathway's lumens or within one or more separate lumens within the multi-lumen pathway. The multi-lumen pathway may comprise one or more single lumen pathways (803 and 806) that may accept either the one or more power channels or the vacuum channel, wherein the one or more single lumen pathways may be combined at some portion with one or more other single lumen pathways to form at least a portion of the multi-lumen pathway (805). In this embodied manner, the one or more power channels may be accepted at different locations from the vacuum channel. Furthermore, in this and similar embodiments, the one or more power channels and the vacuum channel may traverse the distance from the tissue apposition device to their respective sources (for exampled, an electrosurgery generator or a vacuum source) in relative close proximity to one another.

In preferred embodiments, the multi-lumen pathway may comprise a multi-lumen extrusion member, wherein the multi-lumen extrusion may further comprise materials such as plastic or rubber.

Figure 28:
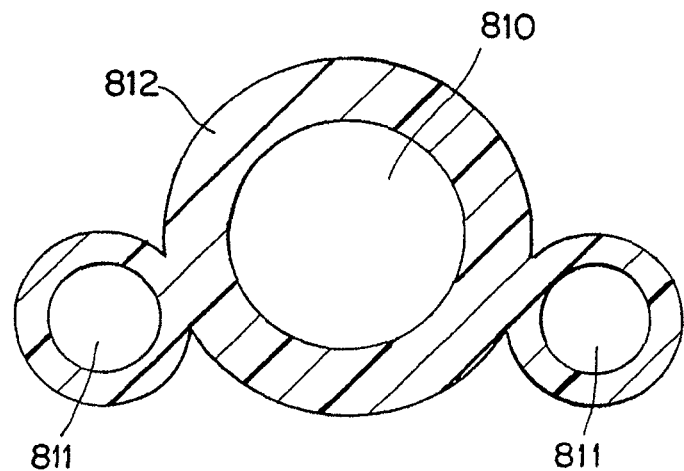
FIG. 28 and FIG. 29 illustrate a cross-sectional view of multiple embodiments of a pathway what may be adapted to accept one or more vacuum channels and one or more power channels.

FIG. 28 illustrates a cross section view of one embodiment of a multi-lumen pathway. The embodiment may comprise a vacuum channel (810) and one or more power channels (811), wherein the vacuum channel (810) and the one or more power channels may be in relative proximity to one another, but they may not occupy the same space as one another. Such an embodiment may comprise one or more pathway walls (812), wherein the one or more pathway walls may be of a material including, but not limited to, rubber or plastic.

Figure 29:
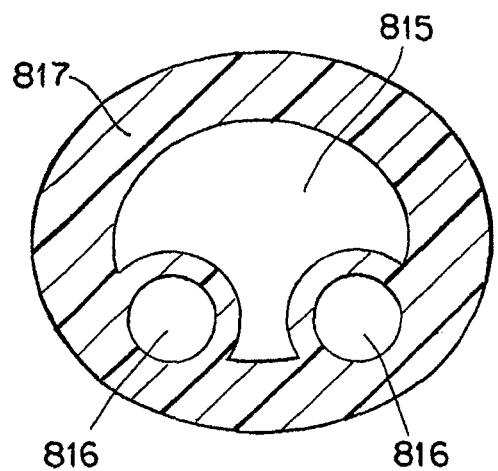

FIG. 29 illustrates a cross section view of another possible embodiment of a multi-lumen pathway. This embodiment may comprise a vacuum channel (815) and one or more power channels (816). The vacuum channel (815) and the one or more power channels (816) may be in relative proximity to one another, wherein the one or more power channels (816) may be disposed such that the one or more power channels occupy space within at least a portion of the vacuum channel lumen (815). Such an embodiment may comprise one or more pathway walls (817), wherein the one or more pathway walls may be of a material including, but not limited to, rubber or plastic.

Certain embodiments of the present invention described herein may be embodied by a tissue apposition device comprising a vacuum cavity having a cavity walls, and one or more energy emitting members or components, wherein the one or more energy emitting members or components are operably coupled to the cavity wall. FIG. 25 illustrates one such embodiment, wherein the energy emitting member is embodied by an electrical circuit comprising a flexible substrate. The electrical circuit may be conformed into a shape and positioned within the vacuum cavity, as illustrated in FIG. 26. However, many other embodiments of the invention are possible.

Energy emitting members or components may be embodied in a plurality of configurations or designs. Some such embodiments may include a variety of features that enhance the performance of the energy emitting member or component. In the case of embodiments that may comprise electrical energy emitting members or components such as a flexible electrical circuit, the configuration of the flexible circuit may provide a plurality of features. For example, the circuit may be adapted to emit monopolar electrical energy or bipolar electrical energy. Furthermore, the circuit may be adapted to emit energy such that it may produce an even distribution of injury to the tissue.

Figure 30:
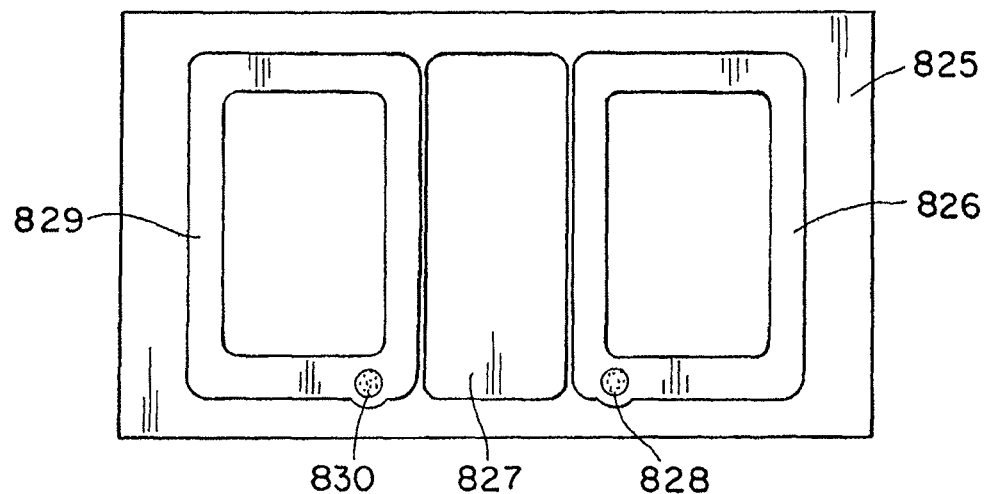
FIG. 30-FIG. 33 are illustrations of different flexible circuit designs.

FIG. 30 illustrates a top view of an embodied flexible circuit configuration similar to the embodiment shown in FIG. 25. This embodiment may comprise one or more layers of material. The layers may comprise non-conductive layers and/or conductive layers. The illustrated circuit may comprise a base layer (825), preferably made of at least a non-conductive or dielectric material, middle layers (826, 829), preferably made of at least a conductive material, and a top layer (827), preferably made of at least a non-conductive or dielectric material. Unlike the embodiment illustrated in FIG. 25, which is preferably configured to emit monopolar electrical energy, the embodiment in FIG. 30 may be configured to emit bipolar electrical energy. Given that middle layer (826) and middle layer (829) may not be in electrical communication with one another (as is the case with the two rectangular frames in the middle layer (771) in FIG. 25, which are in electrical communication with one another via one or more conductive elements (774)). Therefore a bipolar electrical energy emitting configuration may be accomplished with the embodiment in FIG. 30. One example of a bipolar electrical energy emitting configuration may be realized if power channel interface (828) is placed in electrical communication with a power channel of voltage $V_1$ and power channel interface (830) is placed in electrical communication with a power channel of voltage $V_2$. If $V_1$ and $V_2$ are of different values, the voltage differential may drive the bipolar electrical energy emission, which may cause an injury to tissue in close proximity to one or more of the middle layers (826, 829).

Figure 31:
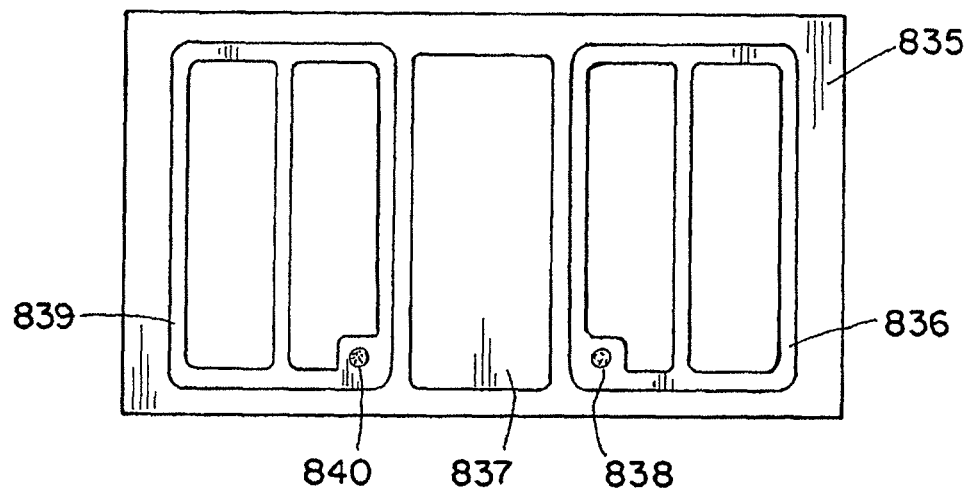

FIG. 31 illustrates a similar embodiment to the embodiment illustrated in FIG. 30. The embodied flexible circuit may comprise a base layer (835), preferable made of at least a non-conductive or dielectric material, middle layers (836, 839), preferably made of at least a conductive material, and a top layer (837), preferably made of at least a non-conductive or dielectric material. The flexible circuit may be configured to emit bipolar electrical energy or monopolar electrical energy. One example of a bipolar electrical emitting configuration may be realized if power channel interface (838) is placed in electrical communication with a power channel of voltage $V_1$ and power channel interface (840) is placed in electrical communication with a power channel of voltage $V_2$. If $V_1$ and $V_2$ are of different values, the voltage differential may drive the bipolar electrical energy emission, which may cause an injury to tissue in close proximity to one or more of the middle layers (836, 839).

While the shape of the middle layers (825, 829) of the embodiment in FIG. 30 is preferably a rectangular frame, the shape of the middle layers (835, 839) of the embodiment in FIG. 31 may preferably be a divided rectangular frame. The divided rectangular frame shape may potentially allow for a more equal distribution of the emitted energy over the tissue in close proximity to the divided rectangular frame. The traces of the divided rectangular frame may allow for a more distributed surface area for which energy to be emitted to the tissue. The distribution of the surface area may lead to an even distribution of the injury to the tissue.

A further embodiment of an energy emitting members, which may be embodied as a flexible circuit, is shown in FIG. 32. This embodiment may be configured to conform to the shape of the vacuum cavity and components that may reside within a vacuum cavity. The flexible circuit may be formed and operably coupled to the cavity wall and components within the vacuum cavity.

Figure 32A:
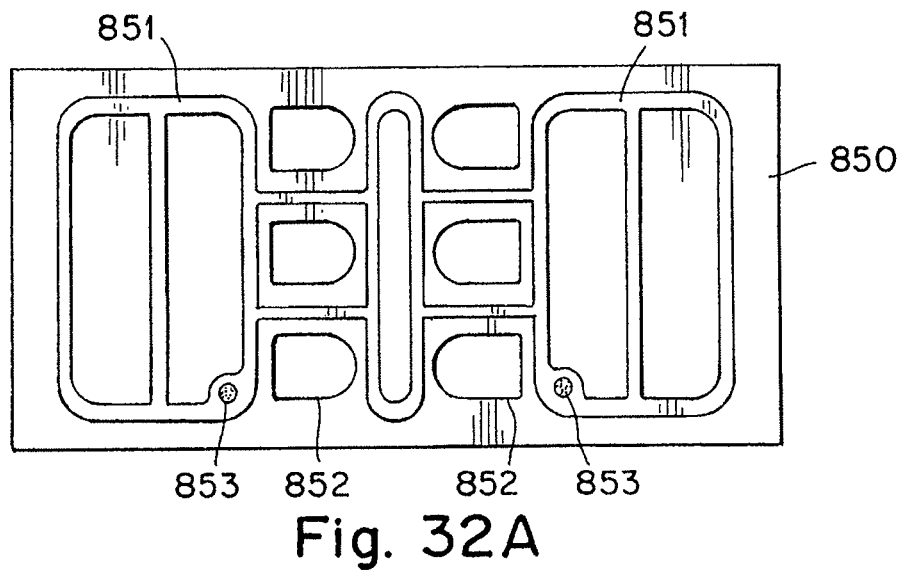

The embodiment may comprise two or more layers of material. FIG. 32A illustrates a top view of an embodied circuit configuration, comprising a bottom layer (850), preferably made of at least a non-conductive or dielectric material, and a top layer (851), preferably made of at least a conductive material. The embodied flexible circuit may be conformed and operably coupled to the vacuum cavity walls and components within the cavity such that the vacuum cavity walls and components within the cavity only come into contact with the bottom layer (850). Therefore, the top layer (851) may be electrically insulated from the cavity walls and components within the cavity. The embodiment shown in FIG. 32 illustrates one such embodiment where the circuit may conform around the vacuum cavity and components within the cavity. Given that the circuit is flexible, the circuit may conform to a variety of shapes. These shapes may allow the circuit to operably couple to the cavity walls and components within the cavity while still electrically insulating the top layer (851). Furthermore, in embodiments that may couple with one or more components within the cavity, such as a vacuum channel, perforations or holes (852) may be disposed in the circuit such that the circuit does not interfere or at least minimizes any interference with the one or more components within the cavity which the circuit is at least partially operably coupled to.

While the embodiment shown in FIG. 32 may be preferably configured for the emission of monopolar electrical energy via a power channel being placed in electrical communication with the power channel interface (853), other embodiments (which are not shown) may be implement, such as embodiments configured for the emission of bipolar electrical energy.

Figure 32B:
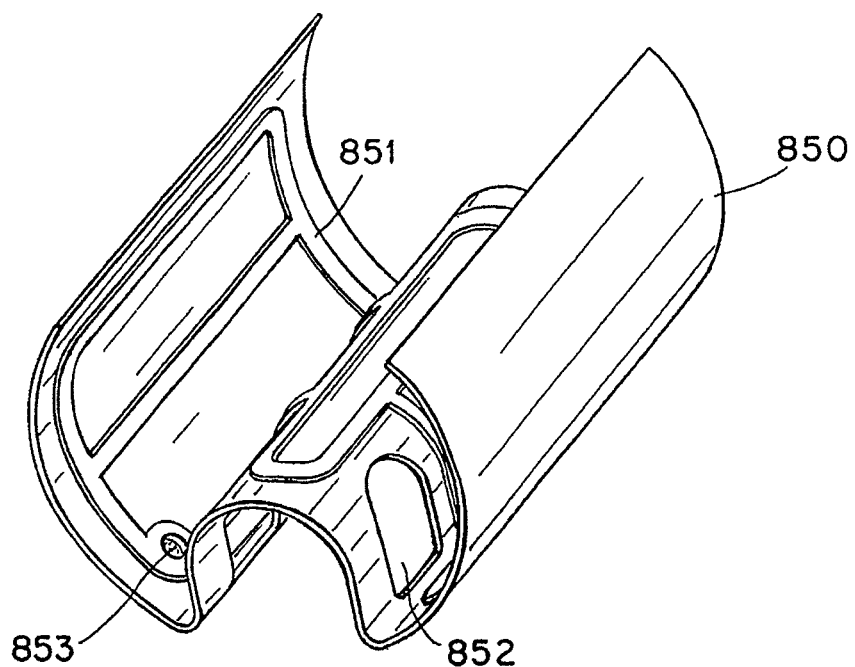
Figure 33:
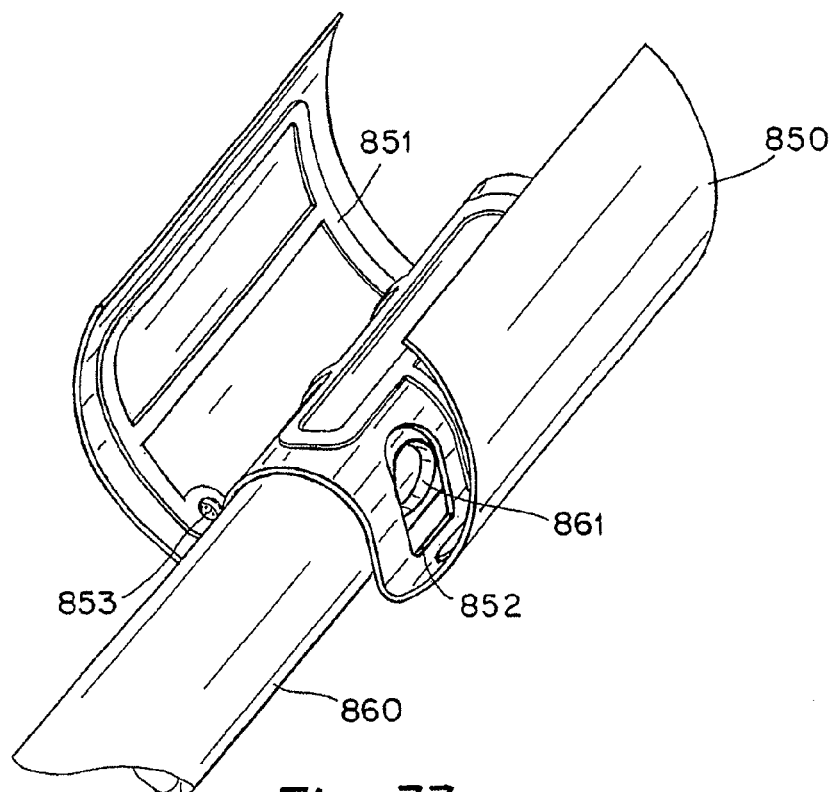

FIG. 32B illustrated the embodied flexible circuit, wherein the circuit is conformed to a shape that may be preferable for operably coupling to the cavity walls and components within the cavity. In this example, the shape may conform around a vacuum channel (860) that may be at least partially present within the cavity. FIG. 33 illustrates the orientation of the conformed flexible circuit as it is coupled over the vacuum channel (860). As illustrated, when the flexible circuit and vacuum channel are oriented to each other, the one or more perforation that may be in the vacuum channel (861) may be lined up with the perforation in the flexible circuit (852), therefore allowing the vacuum channel to operate within little or no hindrance caused by the flexible circuit. More over, the top layer (851), which is preferably made from at least one conductive material, may be electrically isolated from the vacuum channel by the bottom layer (850).

Figure 34:
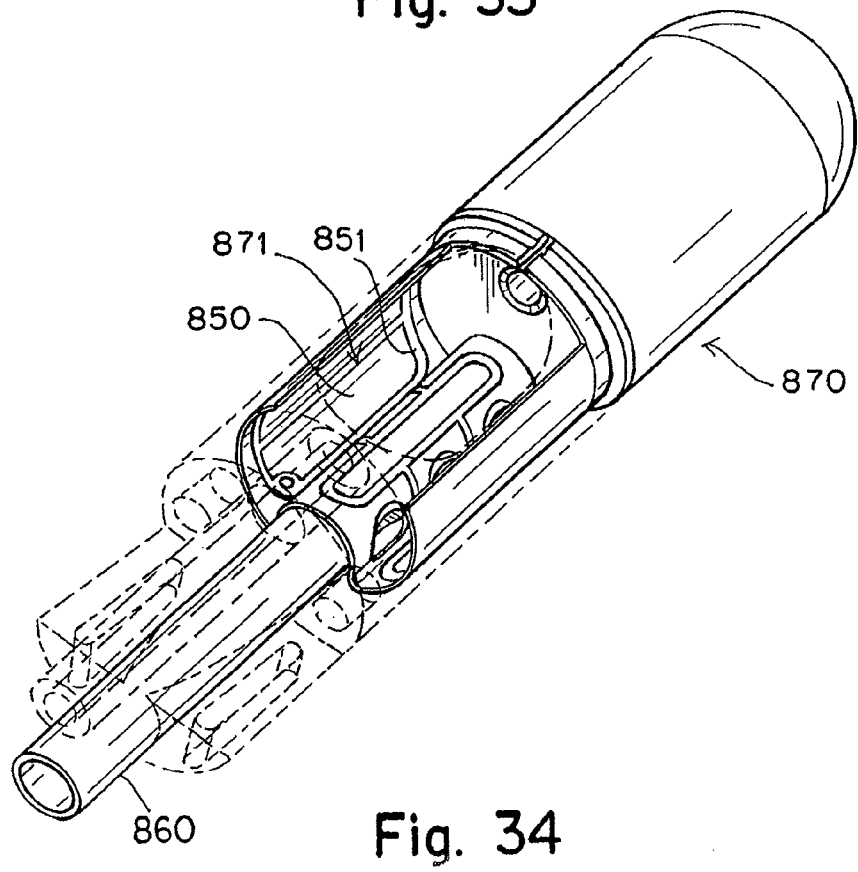
FIG. 34 is an isometric transparent view of a flexible circuit disposed within a vacuum cavity of a tissue apposition device.

FIG. 34 illustrates an isometric view of a tissue apposition device (870) comprising a vacuum cavity with walls, wherein a flexible circuit embodiment (871), such as the embodiment shown in FIG. 33, is operably coupled to the walls of the vacuum cavity. Some portions of the tissue apposition device are displayed as transparent in FIG. 34 for illustrative purposes only. The vacuum cavity further contains at least a portion of a vacuum channel (860), which the flexible circuit is also operably coupled. In preferable embodiments, the flexible circuit may be operably coupled to the walls and components within the cavity such that conductive portions (851) of the flexible circuit may be electrically insulated from the cavity walls and components within the cavity by one or more non-conductive portions (850) of the circuit. When tissue is collected within the vacuum cavity of an embodiment, such as the one illustrated in FIG. 34, the tissue may come into close proximity to the flexible electrical circuit and the conductive portions thereof. Therefore, energy (preferably electrical energy) may be applied or emitted from the conductive portions to the collected tissue to produce injury to the tissue. This may be accomplished as part of a tissue apposition process or procedure.

Figure 35:
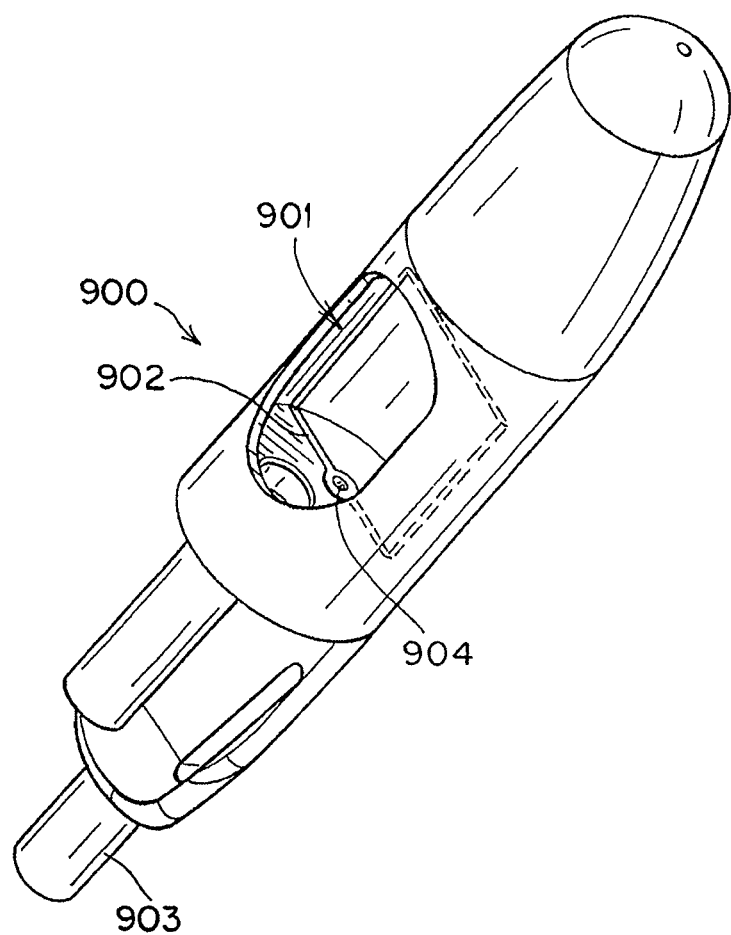
FIG. 35 is an illustration of a tissue apposition device with a wire or strip of conductive material disposed within a vacuum cavity.

Embodiments of inventions described herein may describe tissue appositions devices comprising a vacuum cavity having walls, and one or more energy emitting members or components, wherein the one or more energy emitting members or components further comprise a flexible circuit operably coupled with the vacuum chamber walls. However, other embodiments of the invention are certainly possible. One such embodiment is shown in FIG. 35. In this illustration, a tissue apposition device (900) comprising a vacuum chamber (901) having walls, is demonstrated with an energy emitting member in the form of a wire or strip of conductive material (902). The wire or strip (902) may be of a material including, but not limited to copper, gold, or stainless steel. The wire or strip (902) may be disposed within the vacuum cavity (901) and may be operably coupled to the cavity's walls.

In such embodiments, the tissue apposition device may be positioned in relative proximity to tissue. Vacuum may be applied to the vacuum cavity (901) via a vacuum channel (903) in communication with the vacuum cavity (901), such that a portion of the tissue is collected within the vacuum cavity. As such, the portion of tissue may be in close relative proximity to the energy emitting wire or strip (902). Energy may then be applied to the tissue via the energy emitting member to create injury to the tissue. In preferable embodiments, the energy comprised electrical energy. The energy emitting wire or strip may be in electrical communication with one or more power channels (not shown) via a power channel interface (904).

The embodiment in FIG. 35 illustrates an energy emitting wire or strip in a rectangular shape, but a plurality of different shapes are possible, including a zig-zig pattern. Additionally, embodiments may facilitate both monopolar or bipolar energy emission.

In certain embodiments of a tissue apposition device comprising a vacuum chamber having walls, wherein the vacuum chamber walls may be comprised of a conductive material, a coating, film, and/or layer of non-conductive material may be included to the surface of the walls in order to insulate any energy emitting members from the cavity walls. This coating, film, and/or layer may be of a material including, but not limited to, polyimide or teflon. In such embodiments, the energy emitting member may be operably coupled to the walls of a vacuum chamber, while insulating the energy emitting member and the vacuum chamber walls from one another.

It is, of course, understood that modification of the present invention, in its various aspects, will be apparent to those skilled in the art. Additional method and device embodiments are possible, their specific features depending upon the particular application. For example, embodiments may be possible which comprise a tissue securement device using staples, pins, rods, wires, tags, or magnets to secure the tissue approximation. Additionally, multiple forms of ablation are possible including the combination of one or more forms of ablation to reinforce a tissue apposition. Furthermore, energy emitting members or components may be integrated or coupled to a tissue apposition device in a plurality of means, including material being sputtered or deposited onto one or more surfaces of the tissue apposition device, wherein the component sputtered or deposited onto one or more surfaces may comprise at least a portion of an energy emitting member.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A tissue apposition device comprising:
   a tissue collector having a tissue cavity adapted to collect tissue portions, the tissue cavity including opposing ends spaced apart in a longitudinal direction and a tissue cavity wall extending in the longitudinal direction between the opposing ends, the tissue collector including one or more perforations for applying a vacuum to the tissue cavity;
   a tissue securement device advanceable into the tissue cavity in the longitudinal direction;
   a flexible energy emitter positioned within the tissue cavity and adapted to produce an injury to the tissue, the energy emitter including a flexible electrical circuit operably coupled to the tissue cavity wall, the electrical circuit including a flexible substrate that conforms to the shape of the tissue cavity wall, the flexible substrate including one or more perforations that are aligned with the one or more perforations of the tissue collector to draw a vacuum in the tissue cavity through the one or more perforations in the flexible substrate.

2. The tissue apposition device as in claim 1, wherein the tissue collector includes a vacuum channel adjacent to and in communication with the tissue cavity.

3. The tissue apposition device as in claim 2, wherein the vacuum channel includes the one or more perforations for applying a vacuum to the tissue cavity.

4. The tissue apposition device as in claim 1, wherein the one or more perforations in the flexible substrate include a plurality of perforations.

5. A tissue apposition device comprising:
   a suturing capsule having a tissue suction cavity adapted to capture tissue therein, wherein the tissue suction cavity comprises a tissue suction cavity wall extending in a longitudinal direction, the suturing capsule including one or more perforations for applying a vacuum to the tissue suction cavity;
   a needle slidable through the tissue suction cavity in the longitudinal direction;
   a suture material coupled to the needle; and
   a flexible energy emitter positioned within the tissue suction cavity and adapted to produce an injury to tissue captured in the tissue suction cavity, the energy emitter including a flexible electrical circuit operably coupled to the tissue suction cavity wall, the electrical circuit including a flexible substrate that conforms to the shape of the tissue suction cavity wall, the flexible substrate including one or more perforations that are aligned with the one or more perforations of the suturing capsule to draw a vacuum in the tissue suction cavity through the one or more perforations in the flexible substrate.

6. The tissue apposition device as in claim 5, wherein the electrical circuit includes a non-conductive layer and a conductive layer.

7. The tissue apposition device as in claim 6, wherein the non-conductive layer comprises polyimide and the conductive layer comprises copper.

8. The tissue apposition device as in claim 6, wherein the conductive layer emits electrical energy to produce an injury to the tissue.

9. The tissue apposition device as in claim 8, wherein the conductive layer is configured to produce even distribution of the injury to the tissue.

10. The tissue apposition device as in claim 5, wherein the tissue apposition device further comprises a vacuum channel adjacent to and in communication with the tissue suction cavity.

11. The tissue apposition device as in claim 10 further comprising a power channel in electrical communication with the energy emitter.

12. The tissue apposition device as in claim 11, wherein the power channel is adjacent to the vacuum channel.

13. The tissue apposition device as in claim 12, wherein the power channel is positioned at least partially within the vacuum channel.

14. The tissue apposition device as in claim 10, wherein the vacuum channel includes the one or more perforations for applying a vacuum to the tissue suction cavity.

15. The tissue apposition device as in claim 14, wherein the vacuum channel extends in the longitudinal direction.

16. The tissue apposition device as in claim 5, wherein the one or more perforations in the flexible substrate include a plurality of perforations.

* * * * *